(12) United States Patent
Kang et al.

(10) Patent No.: US 11,506,674 B2
(45) Date of Patent: Nov. 22, 2022

(54) MONOCLONAL ANTIBODY AGAINST D-DIMER AND DIAGNOSIS AGENT FOR DETECTING D-DIMER, CROSSLINKED FIBRIN AND ITS DERIVATIVES CONTAINING D-DIMER BY USING THE ANTIBODY

(71) Applicant: PRINCETON BIOMEDITECH CORPORATION, Monmouth Junction, NJ (US)

(72) Inventors: Jemo Kang, Princeton, NJ (US); Jin Yang, Plainsboro, NJ (US)

(73) Assignee: Princeton BioMeditech Corporation, Monmouth Junction, NJ (US)

( * ) Notice: Subject to any disclaimer, the term of this patent is extended or adjusted under 35 U.S.C. 154(b) by 0 days.

(21) Appl. No.: 15/898,509

(22) Filed: Feb. 17, 2018

(65) Prior Publication Data

US 2019/0011465 A1   Jan. 10, 2019

Related U.S. Application Data

(63) Continuation-in-part of application No. 14/581,500, filed on Dec. 23, 2014, now Pat. No. 9,897,616, which is a continuation of application No. 12/428,321, filed on Apr. 22, 2009, now Pat. No. 8,940,489, which is a continuation of application No. 11/997,247, filed as application No. PCT/KR2005/002491 on Jul. 29, 2005, now abandoned.

(51) Int. Cl.

| | |
|---|---|
| *G01N 33/53* | (2006.01) |
| *C12Q 1/00* | (2006.01) |
| *G01N 33/542* | (2006.01) |
| *C12Q 1/56* | (2006.01) |
| *C12N 5/07* | (2010.01) |
| *C12N 5/16* | (2006.01) |
| *G01N 33/86* | (2006.01) |
| *C07K 16/18* | (2006.01) |
| *C07K 16/36* | (2006.01) |
| *G01N 33/558* | (2006.01) |
| *G01N 33/543* | (2006.01) |
| *C07K 16/26* | (2006.01) |

(52) U.S. Cl.
CPC ............ *G01N 33/86* (2013.01); *C07K 16/18* (2013.01); *C07K 16/26* (2013.01); *C07K 16/36* (2013.01); *G01N 33/54386* (2013.01); *G01N 33/558* (2013.01); *C07K 2317/32* (2013.01); *C07K 2317/92* (2013.01); *G01N 33/5302* (2013.01); *G01N 2333/75* (2013.01); *G01N 2800/224* (2013.01); *G01N 2800/226* (2013.01)

(58) Field of Classification Search
CPC ...... A61K 30/395; A61K 38/08; A61K 38/16; C12Q 1/00; C12Q 1/28; G01N 33/52; G01N 33/536
USPC ......... 424/130.1, 139.1, 141.1, 158.1, 184.1, 424/185.1, 234.1; 435/4, 7.1, 7.9, 13, 435/326, 337
See application file for complete search history.

(56) References Cited

U.S. PATENT DOCUMENTS

| | | | |
|---|---|---|---|
| 4,313,734 A | 2/1982 | Leuvering | |
| 4,758,524 A | 7/1988 | Bundesen et al. | |
| 4,879,217 A | 11/1989 | Petersen et al. | |
| 5,206,140 A | 4/1993 | Marder et al. | |
| 6,541,277 B1 * | 4/2003 | Kang ............... | G01N 33/54366 436/518 |
| 7,374,950 B2 * | 5/2008 | Kang ............... | G01N 33/54386 422/537 |
| 8,940,489 B2 | 1/2015 | Doh et al. | |
| 2002/0160525 A1 * | 10/2002 | Kang ................... | G01N 33/558 436/518 |
| 2008/0274565 A1 * | 11/2008 | Samake ............... | G01N 33/558 436/518 |
| 2012/0028370 A1 | 2/2012 | Nagai et al. | |
| 2015/0301038 A1 * | 10/2015 | Yokokawa ........... | C07K 14/765 436/501 |

FOREIGN PATENT DOCUMENTS

WO    WO 97/09620    *    3/1997

OTHER PUBLICATIONS

Bach-Gansmo et al., "Degradation of Fibrinogen and Cross-Linked Fibrin by Human Neutrophil Elastase Generates D-Like Fragments Detected by ELISA but notLatex D-Dimer Test," Thrombosis Research (Nov. 1998), vol. 92 pp. 125-134.
Bennick et al., "D-Dimer Specific Monocorial Antibodies React with Fibrinogen Aggregates," Thrombosis Research (1996); vol. 82, No. 2, pp. 169-176.
Lawler et al., "Fibrin Fragment D-Dimer and Fibrinogen B beta Peptides inPlasma as Markers of Clot Lysis Dungn Thrombolytic Therapy in Acute Myocardial Infarction," Blood (Oct. 1990); vol. 76, No. 7, pp. 1341-1348.
Laroche et al., "Characterization of a Recombinant Single-Chain Molecule Comprising the Variable Domains f a Monoclonal Antibody Specific for Human Fibrin Fragment D-Dimer," J. Bio. Chem (Sep. 1991); vol. 266, No. 25, pp. 16343-16349.

* cited by examiner

*Primary Examiner* — Gary B Nickol
*Assistant Examiner* — Lakia J Jackson-Tongue
(74) *Attorney, Agent, or Firm* — Fox Rothschild LLP

(57) ABSTRACT

Disclosed are an immunochemical assay device and a method of using the immunochemical assay device for detecting one or more targets or markers such as Cardiac Troponin I, NT-pro-BNP, D-dimer and/or cross-linked fibrin in a fluid sample.

19 Claims, 12 Drawing Sheets

Specification includes a Sequence Listing.

|    | IgG1  | IgG2a | IgG2b | IgG3  | IgM   | IgA   | kapa  | Lamda |
|----|-------|-------|-------|-------|-------|-------|-------|-------|
| B1 | 0.605 | 0.082 | 0.083 | 0.076 | 0.092 | 0.075 | 0.712 | 0.081 |
| B2 | 0.532 | 0.081 | 0.081 | 0.086 | 0.086 | 0.076 | 0.637 | 0.082 |
| B3 | 0.421 | 0.081 | 0.083 | 0.080 | 0.095 | 0.075 | 0.534 | 0.086 |
| B4 | 0.648 | 0.095 | 0.082 | 0.082 | 0.096 | 0.086 | 0.703 | 0.091 |
| B5 | 0.682 | 0.097 | 0.088 | 0.021 | 0.093 | 0.085 | 0.614 | 0.090 |

Beta Chain

```
120        130        140        150        160
 |          |          |          |          |
LKDLWQKRQK QVKDNENVVN EYSSELEKHQ LYIDETVNSN IPTNLRVLRS (SEQ ID NO: 3)

DNENVVN EYSSELEKHQ LYIDETVNSN IPTNLRVLRS 38kDa (SEQ ID NO.: 4)

SSELEKHQ LYIDETVNSN IPTNLRVLRS 37kDa (SEQ ID NO: 5)
```

DNENVVNEY: A epitope region to which B4 monoclonal antibody binds (SEQ ID NO: 1)

Column: 3B6/22  B4        3B6/22        B4
Plasma:  #4    #4    s   #1  2  3    1  2  3

← crosslinked
← Gamma-Gamma Chains

| No. | B4/C3 | | Commercial kit(STAGO) | |
|---|---|---|---|---|
| | -Plasmin | +Plasmin | -Plasmin | +Plasmin |
| 1* | 3.44 | 3.05 | 0.85* | 2.89* |
| 2* | 2.42 | 2.51 | 0.51* | 1.56* |
| 3* | 3.46 | 3.14 | 1.61* | 3.61* |
| 4 | 1.87 | 1.9 | 1.76 | 2.06 |
| 5 | 2.24 | 2.42 | 2.56 | 2.67 |

MONOCLONAL ANTIBODY AGAINST D-DIMER AND DIAGNOSIS AGENT FOR DETECTING D-DIMER, CROSSLINKED FIBRIN AND ITS DERIVATIVES CONTAINING D-DIMER BY USING THE ANTIBODY

CROSS-REFERENCE TO RELATED APPLICATIONS

This application is a Continuation-In-Part application of U.S. patent application Ser. No. 14/581,500, filed Dec. 23, 2014, now U.S. Pat. No. 9,897,616., which is a Continuation filing of U.S. patent application Ser. No. 12/428,321, filed Apr. 22, 2009, now U.S. Pat. No. 8,940,489, which is a continuation filing of U.S. patent application Ser. No. 11/997,247, filed Jan. 29, 2008, now abandoned, which is a national phase filing of International patent application serial No. PCT/KR2005/002491, filed on Jul. 29, 2005, all of which are incorporated herein by reference.

TECHNICAL FIELD

The present invention relates to a monoclonal antibody against a high-molecular cross-linked fibrin including D-dimer and its corresponding epitope produced in a mouse, and an immunochemical assay device for detecting D-dimer and cross-linked fibrin or its derivatives containing D-dimer by using the antibody.

More particularly, the present invention relates to an assay device and a detection method utilizing monoclonal antibody capable of being effectively used as a diagnosis agent for quantifying D-dimer and cross-linked fibrin or its derivatives containing D-dimer since the monoclonal antibody specifically reacts to human D-dimer and is manufactured with a high activity, wherein the monoclonal antibody is derived from a mouse and specifically binds to an amino acid sequence composed of amino acids 134 to 142 from an N terminus of a D domain beta-chain, or amino acids 134 to 142 from the N terminus of the D domain beta-chain and amino acids 124 to 214 of an alpha-chain, and a diagnosis agent for detecting D-dimer and cross-linked fibrin or its derivatives containing D-dimer by using the antibody.

BACKGROUND ART

Blood is regulated by two mechanisms: coagulation and fibrinolysis. The former is a mechanism for forming a thrombus and the latter is a mechanism for dissolving the thrombus. A fibrin is a major component constituting a thrombus and digests into several fibrin degradation products (FDP) through fibrinolysis. The formation and dissolution of fibrin substantially occur at the same times, and D-dimer is an important marker among the FDP produced in fibrin dissolution process. D-dimer is a final degradation product produced when an insoluble fibrin, in which gamma chains are-cross-linked to each other by a factor XIII, is degraded by plasmin. It was known that FDP and D-dimer are detected at a higher concentration in plasma of patients suffering from various diseases such as pulmonary embolism, deep vein thrombosis, tumor surgery, disseminated intravascular coagulation, myocardial infarction, trauma, cancer, kidney and liver function impairment than in healthy humans. In particular, FDP and D-dimer have been the most used markers for diagnosing pulmonary embolism and deep vein thrombosis. Because pulmonary embolism and deep vein thrombosis do not have any distinct symptoms showing that the patients may develop pulmonary embolism and deep vein thrombosis, which eventually may lead to death. Also, only less than 20% of these patients were presented as a real positive through the medical examinations such as pulmonary angiography or venous ultrasonography which is widely practiced method for diagnosing these diseases until now. After introducing D-dimer as a diagnostic marker, up to 40% of the patients who are suspected of having thrombotic diseases can be easily diagnosed as a real patient without undergoing an extensive medical examination. There are many diagnosis agents for detecting a D-dimer such as SimpliRED kit (AGEN), an Asserchrom D-Di kit and an STA-Liatesr D-Di kit using an automation system (Diagnostica Stago), a VIDAS kit (BioMerieux SA, France), etc., but most of the diagnosis agents have common problems of low specificity. Also, test results are significantly different among the diagnosis agents since the different monoclonal antibodies; which adopted in each of the said diagnosis agents recognize different cross-linked fibrin degradation products, for instance, preferential binding of low molecular weight fibrin degradation product or of high molecular fibrin products. Actually, D-dimer level in patient's plasma is affected by various factors such as inflammatory diseases, age of patients, pregnancy, administration of an anti-coagulant, etc. in addition to the thrombosis. In particular, an erroneous diagnosis may be made in some test kits using a diagnosis agent specific to low-molecular weight fibrin degradation products since fibrin derivatives in plasma are present as a partially degraded form of cross-linked fibrin rather than a fully digested D-dimer form, especially in the case of the patients suffering from disseminated intravascular coagulation (DIC) syndrome for a long time and being subject to an anti-coagulation treatment (see Abraham Konberg, Blood 1992, vol 80, No 3, 709-717).

The monoclonal antibody produced in the present invention does not react to fibrinogen of normal human plasma, but specifically reacts to D-dimer produced in degradation of the cross-linked fibrin by plasmin, and cross-linked fibrin or its derivatives containing D-dimer. An ELISA diagnostic method using the monoclonal antibody produced in the present invention had excellent quantitative results than other diagnostic reagents in the test of plasma.

In the present invention, D-dimer-specific monoclonal antibodies were produced from hybridoma cell and purified from the cell culture supernatant, and then applied to the quantification of D-dimer or cross-linked fibrin or its derivatives containing D-dimer in the human body fluids through method of ELISA, LIA, etc.

SUMMARY OF THE INVENTION

Accordingly, the present invention is designed to solve the problems of the prior art, and therefore it is an object of the present invention to provide a murine monoclonal antibody capable of being effectively used as a diagnosis agent for screening and detecting D-dimer and cross-linked fibrin or its derivatives containing D-dimer since the monoclonal antibodies produced are highly reactive to D-dimer.

In order to accomplish the above object, the present invention provides a monoclonal antibody that specifically reacts to D-dimer and cross-linked fibrin or its derivatives containing D-dimer, wherein D-dimer is produced by converting human fibrinogen into fibrin using an enzyme thrombin, followed by digesting with plasmin. The monoclonal antibody of the present invention recognizes D-dimer and cross-linked fibrin or its derivatives containing D-dimer at the same time. D-dimer is produced by completely degrading cross-linked fibrin by plasmin. When an antibody reacts with only low-molecular weight fibrin degradation product, the high molecular weight fibrin degradation product may not be recognized by same antibody. Therefore, the concentration in the samples in which cross-linked fibrin is not degraded or partially degraded may be measured as much lower than their actual level. Thus, it is the most preferred to measure D-dimer level in plasma that the monoclonal antibodies used in D-dimer test recognize the cross-linked fibrin degradation products as well as D-dimer, but does not react with fibrinogen or its derivatives.

The antibody of the present invention preferably reacts to a site including an N-terminal amino acid sequence 134 to 142 of a beta-chain set forth in SEQ ID NO: 1, or a site including an N-terminal amino acid sequence 124 to 214 of an alpha-chain set forth in SEQ ID NO: 2.

Also, the present invention provides a diagnosis agent and an assay device for detecting D-dimer and cross-linked fibrin products, including: a primary antibody that is a monoclonal antibody specifically reacting to D-dimer, or cross-linked fibrin or its derivatives containing D-dimer; and a secondary antibody conjugated with a marker. The monoclonal antibody produced as a secondary antibody binds to the resulting primary antibody and D-dimer complex; and a substrate material for inducing color development by reacting to the marker. The device and method described herein are also applicable to other immunological analysis, simple detection and quantification of biological markers of interest.

BRIEF DESCRIPTION OF THE DRAWINGS

These and other features, aspects, and advantages of preferred embodiments of the present invention will be more fully described in the following detailed description, and accompanying drawings. In the drawings:

In FIG. 1, Lane 1 represents a soluble fibrin, Lane 2 represents α, β and γ chains of fibrinogen, Lane 3 represents a protein size marker (Molecular weight: 250, 150, 100, 75, 50, 37, 25, 15, 10 kDa), Lane 4 represents α, β and γ chains of the separated and purified. D-dimer, and Lane 5 represents an insoluble fibrin.

In FIG. 6, Leftmost lane represents a protein size marker (Molecular weight: 250, 150, 100, 75, 50, 37, 25, 15, 10 kDa), Lane CI represents trypsin-treated D-dimer fragments (Coomassie blue staining), Lane C2 represents chymotrypsin-treated D-dimer fragments (Coomassie blue staining), Lane WB1 represents trypsin-treated D-dimer fragments (Western blotting), and Lane WB2 represents chymotrypsin-treated D-dimer fragments (Western blotting).

In FIG. 8, "s" represents a protein size marker (Molecular weight: 100, 75, 50, 37, 25 kDa), and Arrows represent cross-linked gamma-gamma chains.

DETAILED DESCRIPTION OF THE INVENTION

Figure 1:
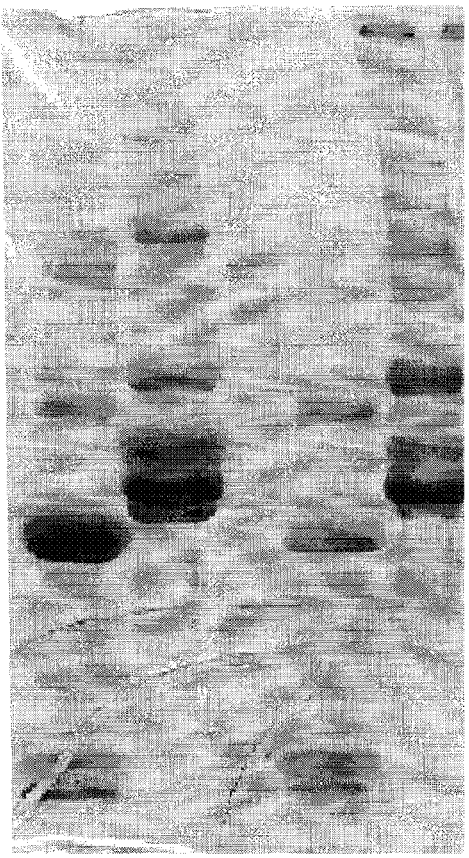
FIG. 1 is a diagram showing a photograph obtained by separating and purifying D-dimer.

Hereinafter, preferred embodiments of the present invention will be described in detail with reference to the accompanying drawings.

The present invention provides a fusion cell line that secrets anti-D-dimer monoclonal antibody, the fusion cell line being obtained by producing D-dimer from human fibrinogen, purifying D-dimer and immunizing a mouse with D-dimer.

A purity of D-dimer protein purified according to the method as described above was determined with the SDS-PAGE.

The fusion cell line producing the monoclonal antibody was prepared by immunizing mouse with D-dimer protein and fusing spleen cells from the immunized mouse with a mouse myeloma cell line. To select a positive clone of the fusion cell line producing the monoclonal antibody of the present invention, an enzyme-linked immunoassay (ELISA) was carried out on the purified D-dimer coated plate for screening, and a limiting dilution was carried out to separate a monoclonal antibody from the selected positive clone of high sensitivity. Finally, the monoclonal antibodies proven to have an anti-D-dimer specificity were named B2, C3, B4 and C5, respectively. The monoclonal antibodies of the present invention produced from the fusion cell line are IgG1-type kappa light chains and have a high specificity to a human D-dimer. Also, the monoclonal antibodies do not exhibit any cross-reactivity to structurally similar fibrinogen and its derivatives. It was found that an antigen recognition region of the monoclonal antibody B4, which is determined by western-blotting to the fragments of the purified D-dimer protein degraded by trypsin, chymotrypsin and CNBr, is composed of sites including N-terminal amino acid sequence 134 to 142 of a beta chain and N-terminal amino acid sequence 124 to 214 of the alpha chain. It was found from the experimental fact that the protein including the N-terminal amino acid sequence 134 to 142 of a beta chain is recognized by the monoclonal antibody B4, while the protein including the N-terminal amino acid sequence 134 to 431 of the beta-chain is not recognized by the monoclonal antibody B4.

Also, a protein encoded by the N-terminal amino acid sequence 124 to 214 of the alpha chain is weakly recognized by the monoclonal antibody B4 in comparison with the total D-dimer protein because the alpha chain and the beta chain are separated far from each other. Therefore, it was confirmed that the monoclonal antibody B4 recognizes a certain region of the unique string structure consist of twisting alpha, beta and gamma chain (see Brown J. H., Proc. Natl. Acad. Sci. USA 2000 97: 85-90; Evers S. J., Biochemistry 1999 38(10): 2941-2946).

Also, the present invention provides a diagnosis agent for screening and detecting D-dimer in plasma and cross-linked fibrin or its derivatives containing D-dimer, using the anti-D-dimer monoclonal antibody produced as described above.

The diagnosis agent of the present invention is composed of the anti-D-dimer monoclonal antibody as a primary antibody; a D-dimer monoclonal antibody produced as a secondary antibody by conjugating a marker such as horseradish peroxidase with the said antibody; and a substrate solution including a material for inducing color development by reacting with the marker.

D-dimer monoclonal antibody used as a secondary antibody conjugate has a marker conjugated thereto. At this time, horseradish peroxidase (HRP), alkaline phosphatase, and other suitable markers may be used. The presence of the D-dimer antigen may be determined by the binding of the antigen present in the sample to a primary antibody immobilized on solid surface. Secondary antibody conjugate then forms a sandwich complex.

The substrate solution for inducing color development by reacting with the marker includes a buffer and a coupler such as o-phenylenediamine, hydrogen peroxide solution, etc. The substrate solution may develop colors by reaction of the marker conjugated to the monoclonal antibody, and therefore the presence and an amount of the antigen may be determined by measuring a level of the color development.

Ultimately, the concentration of D-dimer or high molecular weight cross-linked fibrin degradation product in tissue sections, whole blood, plasma, cells or like may be quantitatively analyzed with the diagnosis agents on the crude samples themselves or by using ELISA, western blotting, immunoprecipitation or like.

Another aspect of the invention provides an immunochemical assay device. The device generally includes a base member and an array disposed on the base member. The array includes a reservoir pad, a wicking membrane, a dye zone, and an assay indicia zone. Two or more zones or pads can be integrated into a single zone or pad. For example, a reservoir pad, a dye zone and a filter zone can be combined in any way among any two or three of them. Alternatively, a pad or zone may be divided into multiple sub-pads or sub-zones.

The device is suitable for the detection of targets including but not limited to biological markers, disease state markers (e.g. cancer makers or any surrogate biomarkers associated with various disease states for cancer, infectious disease and metabolic states), extract of tissue (e.g. suspected cancer tissue), and chemicals (e.g. antibiotics and growth hormone in milk, egg, meat or other food; pesticide or herbicide in fruits and vegetables). In some embodiments, the target is D-dimer, cross-linked fibrin or derivative thereof.

Multiple targets can be detected in the same sample. Exemplary sets of targets include: Cardiac Troponin I and D-Dimer; Cardiac Troponin I and NT-pro-BNP; Troponin I, NT-pro-BNP and D-dimer (TnI, NT-pro-BNP and D-dimer). In some embodiments, two or more immunochemical components (e.g. antibody) specific to a target (e.g. TnI, NT-pro-BNP, and D-dimer) binds a different epitope of target antigen instead of competing for the same binding site. The device of the present invention thus allows the comprehensive detection of disease markers. For example, the device can be applied to early detection of cardiac diseases when used in an SOB Cardiac panel test.

The reservoir pad is impregnated therein a first immunochemical component conjugated to a first label. The first immunochemical component is capable of specifically binding to a target of interest in the sample to form an immuno-complex. The dye zone is impregnated therein a second immunochemical component conjugated to an indicia label, wherein the second immunochemical component is capable of specifically binding to the target of interest. The first and second immunochemical components are the same or different. The target of interest forms a sandwich-shaped complex with the first and second immunochemical components.

The reservoir pad has sufficient porosity and volume to receive and contain a fluid sample upon which an assay is to be performed. The wicking membrane is disposed distally to the reservoir pad, and has sufficient porosity and volume to absorb a substantial proportion of the sample received in the reservoir pad. In some embodiments, the dye zone is separate and distinct from the reservoir pad and wicking membrane, and interposed between and in fluid communication with the wicking membrane and the reservoir pad.

In some embodiments, the reservoir pad and/or the dye zone are operable to permit passage of the immuno-complex to the wicking membrane, while impeding passage of larger components contained in the sample. In some embodiments, the reservoir pad and/or the dye zone are divided in two or more subzones, at least one of which functions to permit passage of the immuno-complex to the wicking membrane, while impeding passage of larger components. In some embodiments, the first label is biotin and the immobilized substance is avidin. In some embodiments, the reservoir and the dye zone incorporate the same porous fiber material such as glass fiber or any such material treated to be hydrophilic.

In some embodiments, the reservoir pad and the dye zone are constructed in two separate pads which can be placed in one plane, stacked vertically or positioned in any other suitable configuration. In some embodiments, the reservoir pad and the dye zone are integrated into a single pad, where the first and second immunochemical components overlap with each other or are distributed in different sub-zones of the same pad. The target of interest can first come into contact with the first immunochemical component, the second immunochemical component, depending on the specific configuration of the device.

For example, the reservoir pad and the dye zone can be incorporated into a single pad with a particular configuration so that the dye zone contacts the fluid sample first. Further, the reservoir pad can also function to impede passage of larger components or filter off interfering components from the sample.

The device can also include on the base member a filter zone or blood separation zone, which permits passage of any specific immuno-complex in said sample, but impeding passage of larger components contained in the sample. This filter zone or blood separation zone can be distinct from the above mentioned the reservoir pad and the dye zone. Alternatively, this filter zone or blood separation zone can be integrated into one or both of the reservoir pad and the dye zone.

The assay indicia zone is disposed in the wicking membrane, wherein an immobilized substance is disposed in the assay indicia zone of the wicking membrane downstream of the reservoir pad for providing an assay indication. The immobilized substance is specific to the first label in the immuno-complex contained in the sample to form assay indicia. The assay indicia contains the indicia label, which serves as a detectable probe.

The wicking membrane can be made from any suitable porous material with sufficient porosity to allow access by detection antibodies and/or antigens and a suitable surface affinity to bind antigens and/or antibodies. Microporous structures, in general, are preferred, but materials with gel structure in the hydrated state may be used as well. Such useful solid supports include, but are not limited to, nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), porous polyethylene frit or pads, and glass fiber filter paper; either used by themselves or in conjunction with other materials.

In some embodiments, the wicking membrane comprises microporous membrane material selected from the group consisting of nylon, cellulosic material, polysulfone, polyvinylidene difluoride, glass fiber, polyester, and combinations thereof. In some embodiments, the wicking membrane comprises nitrocellulose material.

The second immunochemical component in the dye zone is conjugated to an indicia label. In some embodiments, the indicia label is metallic colloidal gold sol, fluorescent dye, chromogenic dye encapsulated micro-particles or fibers (e.g. fluorescent or chromogenic dye encapsulated polystyrene beads, dyed polymeric cellulose fiber), fluorescent dye encapsulated polystyrene microbeads, reactive dye coupled polymeric molecules (e.g. dyed dextran), or any combination of these. In some embodiments, the second immunochemical component is conjugated to only one label (e.g. metallic colloidal gold sol).

The first immunochemical component and the second immunochemical component can be the same or different. In some embodiments, each of the first immunochemical component and the second immunochemical component independently binds to a site including a) amino acid residues 134th to 142nd from N-terminal region of a beta-chain, set forth in SEQ ID NO: 1; or b) amino acid residues 124th to 214th from N-terminal region of a beta-chain, set forth in SEQ ID NO: 2.

In some embodiments, the first immunochemical component and the second immunochemical component are each an antibody.

The device can also include a control zone disposed in the wicking membrane downstream of the indicia zone. A third immunochemical component is immobilized in the control zone. When any unbound or excess second immunochemical component flow to the control zone, it binds to the third immobilized immunochemical component to form control assay indicia. In some embodiments, the third immunochemical component is a sheep or goat anti-mouse IgG antibody. In some embodiments, the third immunochemical component is specific to the second immunochemical component.

The device can be used for the detection of one or more targets of interest in the same sample. Specifically, the first immunochemical component in the reservoir pad includes 2, 3, 4 or more types of immunochemical components, each of which is capable of specifically binding to a target of interest. For example, the first immunochemical component includes two types of immunochemical components (coded as 1A and 1B), which bind specifically to D-dimer (or cross-linked fibrin, or derivative thereof) and a heart failure marker (e.g. NT-pro-BNP), respectively. Immunochemical components 1A and 1B are each conjugated to a label, which can be the same or different (coded as label A and label B, etc). The different types of the first immunochemical components can be in the same zone or pad. Alternatively, they can be in separate zones, or in partially overlapped zones.

Similarly, the second immunochemical component in the dye zone includes 2, 3, 4 or more types of immunochemical components, each of which is capable of specifically binding to a target of interest. For example, the second immunochemical components 2A and 2B bind specifically to D-dimer (or cross-linked fibrin, or derivative thereof) and a heart failure marker (e.g. NT-pro-BNP), respectively. Each of the different types of the second immunochemical components is conjugated to a different indicia label (e.g. metallic colloidal gold sol as indicia label A and fluorescent dye as indicia label B). The different types of the second immunochemical components can be in the same zone or pad. Alternatively, they can be in separate zones, or in partially overlapped zones.

Further, the immobilized substance in the indicia zone can be the same or different (e.g. 2, 3, 4, or more types coded as substance A, substance B, substance C, substance D, etc, each type binding to the respective type of the first immunochemical component). After the first and second the third immunochemical components bind to a target of interest and form a sandwich-shaped complex, the complex is captured in the indicia zone due to the binding of the immobilized substance to the first label of the first immunochemical component. Different complexes comprising different targets of interest are captured in the indicia zone this way. Because each complex features a unique indicia label, the identity or amount of the associated target can be detected readily. The different types of immobilized substances can be immobilized in the same zone or pad.

In some embodiments, the different types of the substances are immobilized in separate indicia zones, each corresponding to a different target of interest. Accordingly, the labels on the different types of the first immunochemical components are also different (e.g. Label A, Label B, etc.) and the different labels will specifically bind to a respective type of the immobilized substances. Therefore, different targets will be detected at different indicia zones.

The device can also include a control zone as described above, wherein a third immunochemical component is immobilized. Any excess or unbound second immunochemical component can be detected via the indicia label after binding to the third immunochemical component. The control zone for different types of second immunochemical components can be the same or different. In some embodiments, different types of the second immunochemical components can have different control zones, which contain different types of the third immunochemical component (e.g. type 3A in zone 1, 3B in zone 2, 3C in zone 3, etc.) for binding specifically to the respective type of the second immunochemical component.

In a second type of embodiments, the device includes a base member and an array disposed on the base member. The array includes (i) a reservoir pad having sufficient porosity and volume to receive and contain a fluid sample upon which an assay is to be performed;

(ii) a wicking membrane disposed distally to the reservoir pad. The wicking membrane has sufficient porosity and volume to absorb a substantial proportion of the sample received in the reservoir pad;

(iii) a dye zone impregnated therein a first immunochemical component conjugated to an indicia label, wherein the first immunochemical component is capable of specifically binding to the target of interest in the sample to form an immuno-complex, further wherein the target of interest is a biological marker, a disease state marker, or an extract of tissue. The indicia label and the target of interest can be the same as any of the embodiments described in this patent document. and (iv) an assay indicia zone disposed in the wicking membrane, wherein an immobilized substance comprising a second immunochemical component capable of specifically binding to the target of interest is immobilized. The first immunochemical component and the second immunochemical component can be the same or different. In some embodiments, each of the first immunochemical component and the second immunochemical component independently binds to a site including a) amino acid residues 134th to 142nd from N-terminal region of a beta-chain, set forth in SEQ ID NO: 1; or b) amino acid residues 124th to 214th from N-terminal region of a beta-chain, set forth in SEQ ID NO: 2.

In this second type of alternative embodiments, the device can also include a control zone disposed in the wicking membrane downstream of the indicia zone, wherein a third immunochemical component is immobilized in the control zone, and binding of the third immobilized immunochemical component to unbound or excess first immunochemical component forms control assay indicia. In some embodiments, the third immunochemical component is a sheep or goat anti-mouse IgG antibody.

The indicia label is as described above. In some embodiments, the indicia label is indicia label is selected from the group consisting of metallic colloidal gold sol, fluorescent dye, and chromogenic dye encapsulated micro-particles.

The device can also be used for the detection of one or more targets of interest in the same sample. Specifically, the first immunochemical component in the dye zone includes 2, 3, 4 or more types of immunochemical components, each of which is capable of specifically binding to a target of interest. For example, the first immunochemical component includes two types of immunochemical components (coded as 1A and 1B), which bind specifically to D-dimer (or cross-linked fibrin, or derivative thereof) and a heart failure marker (e.g. NT-pro-BNP), respectively. Immunochemical components 1A and 1B are each conjugated to an indicia label, (coded as indicia label A and indicia label B). The different types of the first immunochemical components can be in the same zone or pad. Alternatively, they can be in separate zones, or in partially overlapped zones.

Further, the immobilized second immunochemical component in the indicia also have different types (e.g. 2, 3, 4, or more types coded as 2A, 2B, 2C, 2D, etc, each type binding specifically to a respective target). In some embodiments, a first immunochemical component and a second immunochemical component (e.g. 1A and 2A) each bind a different epitope of target antigen instead of competing for the same binding site. In some embodiments, the different types of second immunochemical components are immobilized in the same zone. In some embodiments, the different types of second immunochemical components are immobilized in different zones.

In this second type of alternative embodiments, the device can also include a control zone disposed in the wicking membrane downstream of the indicia zone, wherein a third immunochemical component is immobilized in the control zone, and binding of the third immobilized immunochemical component to unbound or excess first immunochemical component forms control assay indicia. In some embodiments, the third immunochemical component is a sheep or goat anti-mouse IgG antibody. The control zone for different types of first immunochemical components can be the same or different. In some embodiments, different types of the first immunochemical components have different control zones, which contain different types of the third immunochemical component (e.g. type 3A in zone 1, 3B in zone 2, 3C in zone 3, etc.) for binding specifically to the respective type of the first immunochemical component.

Other components of the device are similar or the same as in the above described embodiments.

In a third type of alternative embodiments, the device includes a base member and an array disposed on the base member. The array includes (i) a reservoir pad having sufficient porosity and volume to receive and contain a fluid sample upon which an assay is to be performed;

(ii) a wicking membrane disposed distally to the reservoir pad. The wicking membrane has sufficient porosity and volume to absorb a substantial proportion of the sample received in the reservoir pad;

(iii) a dye zone impregnated therein a first immunochemical component conjugated to an indicia label, wherein the first immunochemical component is a peptide antigen comprising amino acid residues $134^{th}$ to 142(a) or amino acid residues $124^{th}$ to $214^{th}$ (b) from N-terminal region of beta-chain. The indicia label is as described above in any of the other embodiments.

(iv) an assay indicia zone disposed in the wicking membrane, wherein an immobilized substance comprising a second immunochemical component capable of specifically binding to the target of interest is immobilized. In some embodiments, the second immunochemical component is an antibody. In some embodiments, the second immunochemical component binds to a site including a) amino acid residues 134th to 142nd from N-terminal region of a beta-chain, set forth in SEQ ID NO: 1; or b) amino acid residues 124th to 214th from N-terminal region of a beta-chain, set forth in SEQ ID NO: 2.

In this third type of embodiments, the probe labeled antigen compete against the target of interest (e.g. natural D-dimer) in a clinical sample for the same binding site of the antibody. In some embodiments, only one antibody of choice would be utilized in the competition assay. In the absence of target marker (e.g. D-dimer) in the sample, maximum amounts of the labeled antigen will be binding to the antibody capture on the test line, while the signal from the indicia label decreases due to presence of the target in the sample. For example, the signal from a gold label may decrease proportionally relative to the amount of the D-dimer in the sample. The third type of embodiments can also include a control zone, wherein a third immunochemical component is immobilized in the control zone, and binding of the third immobilized immunochemical component to unbound or excess first immunochemical component forms control assay indicia.

In any of the above described embodiments, the reservoir pad and the dye zone can be separate from each other or integrated into a single pad. The device can also include a filter zone or blood separation zone which can be distinct and separate from the reservoir pad and the dye zone. Alternatively, this filter zone or blood separation zone can be integrated into one or both of the reservoir pad and the dye zone.

In some embodiments, the target of interest is D-dimer and/or cross-linked fibrin. In some embodiments, the first immunochemical component and the second immunochemical component are each an antibody and independently bind to a site including a) amino acid residues 134th to 142nd from N-terminal region of a beta-chain, set forth in SEQ ID NO: 1; or b) amino acid residues 124th to 214th from N-terminal region of a beta-chain, set forth in SEQ ID NO: 2.

The device can be in any suitable form or shape. For example, a device in the form of a cassette can have windows for sample application and signal detection.

Various types of indicia labels can be used in any embodiment of the present invention. Examples include, but are not limited to, chromogens; catalysts; fluorescent compounds; chemiluminescent compounds; radioactive elements; colloidal metallic (such as gold), non-metallic (such as selenium) and dye particles; enzymes; enzyme substrates; organic polymer latex particles, liposomes or other vesicles containing such signal producing substances; etc. A large number of enzymes suitable for use as labels include, but are not limited to, phosphatases and peroxidases, such as alkaline phosphatase and horseradish peroxidase which are used in conjunction with enzyme substrates, such as nitro blue tetrazolium, 3,5',5,5'-tetranitrobenzidine, 4-methoxy-1-naphthol, 4-chloro-1-naphthol, 5-bromo-4-chloro-3-indolyl phosphate, chemiluminescent enzyme substrates such as the dioxetanes, and derivatives and analogs thereof. Fluorescent compounds such as fluorescein, phycobiliprotein, rhodamine and the like, including their derivatives and analogs are suitable for use as labels.

A further aspect of the invention provides a system including the assay device described above. The system may further includes a detector for detecting a signal from the indicia zone. In some embodiments, the system includes a camera for recording the image or color of the signal, the intensity of which corresponds to the amount of the target component to be detected. For example, by comparing the color intensity with a reference or standard, the amount of the D-dimer can be readily qualitatively or quantitatively determined. In some embodiments, the signal is wirelessly transmitted to a processor (e.g. a computer).

The detector or reader can include one or more of the following components/steps:

a) a test card housing and tray that can be slide in or out of the reader under the camera housing;

b) a housing to contain LED light source over the test cassette when the test is started and the tray is in;

c) a sensitive CCD or CMOS (complementary metal-oxide-semiconductors) camera lenses close over the cassette;

d) a programed mechanism to take 32 real images over 2 second when the reading time is up and normalize to cancel out any abnormal background and integrate the intensity of the line;

e) programmed computation of the concentration of the analyte(s) detected against the set standard curve equation;

f) a reporting mechanism (e.g. printing out to the results);

g) command and control screen via interactive touch screen command on the reader from start of the reader QC at the beginning of the use for a given day to final report of the assay results;

h) a transmittor capable of wirelessly transmitting the results to main command terminal via for example blue tooth, or Wi-Fi or thru a simple RS_232_connection;

i) a communication component capable of inputting remote command by supervisor and allowing for data retrieval and report to predestinated terminal;

j) an auto calibration process to maintain uniform reading results from day to day and from site to site over entire reading dynamic ranges;

k) detecting emission light intensity of fluorescent excitation of fluorescence probe label;

l) internal heating and/or cooling to maintain uniform ideal assay temperature during operation;

m) a sensor for monitoring room temperature and capable of normalizing the assay signal to the pre-established and programmed standard values of reading of the standard curve at the pre-set temperature;

Alternatively and/or additionally, the system may further include a computer-readable non-transitory medium that contains software program instructions such as computer programs written in C, C++, Java or other computer languages. The program instructions can be executed on a computer, to operate a detector, reader or scanner to be able to detect the signal of the indicia label and communicate such information to a processing unit for processing the data. The processing unit may be co-located with the computer that runs the program instructions, may be co-located with the reader or scanner, or may be a remote computer on either a server or client device that is in wireless communication with the reader or scanner. The program instructions may further cause the processing unit to compare the detected signal communicated by the scanner with the information about one or more references stored in the database, and identify a disease or the risk of developing a disease. A software program may be incorporated into the scanner or data processing unit/device.

The system may further include a database, which includes information of a reference or a standard. By comparing a detected signal/target level with a reference or a standard, a disease or risk of having a disease in a subject (human or animal) can be readily determined.

A further aspect of the invention provides a method of detecting and/or quantifying various types of biological markers, disease state markers in the body fluid (e.g. blood, plasma, serum, sputum, stool, tears, mucus, urine, effusions, amniotic fluid, and ascitic fluid), extracts of tissue (e.g. tumor tissue, organ tissue), chemicals (e.g. pesticides or pollutants in food), or other targets of interest with the assay device described herein. If necessary, modifications or adoptions of the reagents and/or immunological binding partners can be made to suit the specific needs of the detection or quantification. In some embodiments, the target of interest is D-dimer and/or cross-linked fibrin in a fluid sample. Non-limiting examples of the fluid sample include blood, plasma, serum, sputum, stool, tears, mucus, urine, effusions, amniotic fluid, ascitic fluid and any clinical sample.

The method is applicable to the qualitative or quantitative detection of D-dimer and/or cross-linked fibrin as well diseases (e.g. thrombotic diseases) associated with this biomarker. Non-limiting examples of diseases associated with D-dimer and/or cross-linked fibrin include disseminated intravascular coagulation (DIC), deep vein thrombosis (DVT), pulmonary embolism (PE), various thrombosis.

The method generally includes the steps of
a) depositing a fluid sample to the reservoir pad of an assay device of the present invention;
b) maintaining the assay device under conditions which are sufficient to allow said D-dimer and/or cross-linked fibrin to bind to said first immunochemical component, forming a specific binding complex, and to allow said fluid to transport said specific binding complex by capillary action through the membrane strip to the indicia zone;
c) maintaining the assay device under conditions which are sufficient to allow the specific binding complex in the fluid to bind to the immobilized substance; and
d) detecting a signal from the indicia label.

In some embodiments, the target to be detected is present in the sample ranging between about 0 and about 20,000 ng/mL. In some embodiments, the target ranges between about 0 and about 10,000 ng/mL. In some embodiments, the target ranges between about 0 and about 6,000 ng/mL. In some embodiments, the target ranges between about 50 and about 8,000 ng/mL. In some embodiments, the target ranges between about 60 and about 5,000 ng/mL. In some embodiments, the target is D-dimer and/or cross-linked fibrin.

The method may also include a step of comparing the signal with a reference to determine the level of the target of interest. For example, the intensity of the signal reflects the amount or concentration of a particular biomarker in the sample. In some embodiments, the method is useful for detecting a thrombosis disease or a risk of developing a thrombosis disease in a subject (human or animal). For example, a rise in the level of D-dimer and/or cross-linked fibrin can be an indication of a thrombosis disease or a risk of having the thrombosis disease in an individual. Non-limiting examples of thrombosis diseases include disseminated intravascular coagulation (DIC), deep vein thrombosis (DVT), and pulmonary embolism (PE).

Alternatively and/or additionally, the kit may further include a computer-readable non-transitory medium that contains software program instructions such as computer programs written in C, C++, Java or other computer languages. The program instructions can be executed on a computer, to operate a scanner to be able to detect the distinguishable feature of the indicium and communicate such information to a processing unit for processing the data. The processing unit may be co-located with the computer that runs the program instructions, may be co-located with the scanner (such as embedded inside the scanner), or may be a remote computer on either a server or client device that is in wireless communication with scanner. The program instructions may further cause the processing unit to compare the detected distinguishable feature communicated by the scanner with the information about one or more distinguishable features of the indicium stored in the database, and identify relative positions of sections cutting through the indicium. The present invention also provides a system which contains the above described mold and software program. The software program may be incorporated into the scanner or data processing unit/device.

As described above, the device can include additional components and can be manufactured in different forms and formats. Therefore, additional steps can be incorporated accordingly. For example, allowing unused monoclonal antibody wick further downstream and binds to control line of sheep or goat anti-mouse antibody shows that the testing procedure is done properly and all reagents work in accordance to the design.

Hereinafter, preferred embodiments of the present invention will be described in detail.

However, it should be understood that the description proposed herein is just a preferable example for the purpose of illustrations only, not intended to limit the scope of the invention.

Example 1: Preparation and Purification of Human D-Dimer Protein

As an antigen D-dimer was obtained by converting human fibrinogen into fibrin using an enzyme thrombin, cutting fibrin with an enzyme plasmin and purifying the resultant fragments of fibrin. That is to say, a reaction buffer was prepared by dissolving 50 mM Tris-HCl (p117.5), 0.1M NaCl and 16 mM $CaCl_2$ and adding 5% human plasma as a source of Factor XIII Bovine thrombin was added at an amount of 500 unit per 1 g of fibrinogen and reacted at room temperature for 16 hours to form a fibrin mass, and then fibrin mass was immersed in 2% acetic acid solution for 16 hours to remove un-cross-linked fibrin. Fibrin mass was thoroughly washed with distilled water, frozen with liquid nitrogen, milled, and then put into a reaction buffer. 1 unit of urokinase was added to 1 unit of plasminogen, and the resultant mixture was reacted at 37° C. for 30 minutes to form an active plasmin. Then, 1 unit of plasmin per 500 mg of fibrin was added, put into a reaction buffer, and reacted at 37° C. for 72 hours while adding 1 unit of the active plasmin every 24 hours. After 72-hour reaction, 400 unit of aprotinin was added to stop the reaction. It was confirmed that D-dimer was produced since a cross-linked gamma chain was observed near a band of 80 kDa in SDS-PAGE (FIG. 1).

Gel permeation chromatography was used to purify D-dimer from the produced fibrin degradation products. At this time, the buffer used is 50 mM phosphate solution (pH7.5) containing 6M urea, and the gel permeation chromatography was carried out according to the method proposed by Olexa S A, and Budzynski A Z, et al. (Proc Natl Acad Sci USA., 1980, March 77(3): 1374-1378) was confirmed that D-dimer was separated and purified using SDS-electrophoresis and ELISA, and D-dimer having a purity of at least 90% was used as an antigen (FIG. 1).

Example 2: Preparation of Fusion Cell Line Producing Monoclonal Antibody Specific to D-Dimer In order to prepare a fusion cell line that produces a monoclonal antibody, an 8-week-old experimental female mouse (BALB/c mouse) was immunized, as follows. Firstly, 50 µl of D-dimer protein, expressed and purified in Example 1, was mixed at the same volume with 150 µl of complete Freund's adjuvant (Sigma) to prepare an emulsifying solution, and then the emulsifying solution was peritoneally administered to a BALB/c mouse. After the first administration, D-dimer protein was emulsified in incomplete Freund's adjuvant (Sigma) at the same amount, and then the resultant emulsifying solution was peritoneally injected to a BALB/c mouse upon the first and second administrations every 10 days, and 20 µg of D-dimer protein was injected upon the third and fourth peritoneal administrations to stimulate a specific immune reaction. Finally, only 20 µg of D-dimer protein was peritoneally administered to a BALB/c mouse at 3 days before a fusion cell line was prepared completely. In order to prepare a fusion cell line, a spleen cell was taken from the immunized mouse, and mixed with mouse myeloma cell line Sp2/0-Ag14 (ATCC, U.S.) at a cell ratio of 2:1. Then, the cell mixture was centrifuged to remove a supernatant, and then 1 ml of PEG-1500 (polyethylene glycol-1500, Boehringer Mannheim) was added and thoroughly mixed for 1 minute using a plastic Pasteur pipette, and 15 ml of a serum-free DMEM culture solution (Gibco) was added dropwise over 10 minutes and thoroughly mixed, and then the same volume of DMEM medium containing 20% fetal bovine serum was added and kept at 37° C. for 30 minutes. The cell suspension was centrifuged, and the precipitated cell pellet was added to a DMEM medium containing 20% fetal bovine serum again, and the resultant mixture was divided at an amount of 100 µl into a 96-well plate, and incubated overnight at 37° C. under a 5% $CO_2$ atmosphere condition. After 1-day incubation, a 2×HAT medium (Sigma) was added at an amount 100 µl to each plate and incubated to form colonies. After the colonies were then formed, an enzyme-linked immunoassay (ELISA) was carried out using the purified D-dimer to select positive colonies, but to exclude the positive colonies against fibrinogen and its derivatives.

In particular, the purified D-dimer and fibrinogen and its derivatives, respectively, were thoroughly mixed in a coating buffer (0.1M Na-carbonate, pH 9.5), added at an amount of 1 µg to each 96-well ELISA plate (Maxisorp, Nunc), and then reacted overnight at 4° C. In the next day, a blocking buffer (1% bovine serum albumin/PBS) was added and kept at room temperature for 2 hours. Then, the solution was removed off, each of the wells was washed with a washing solution, a culture solution of the fusion cell line was added at an amount of 100 µl to each well and reacted at 37° C. for 1 hour. Then, an excessive amount of the non-reacted antibody was removed off, goat-derived anti-mouse IgG antibody (KPL) to which horseradish peroxidase (HRP) binds, o-phenylenediamine (Sigma) which is a substrate of HRP, and hydrogen peroxide solution ($H_2O_2$) was sequentially added to confirm whether or not the specifically bound antibody is present in the culture solution. As a result, the hybridoma clones, which exhibit the reactivity to D-dimer protein but do not react to fibrinogen and its derivatives, were selected as positive clones that secret the antibody against D-dimer.

A limiting dilution was carried out to separate a monoclonal clone from the positive clones selected in the above-mentioned procedure.

For this purpose, all of the cell lines present in the 96-well plate were taken and suspended to count the cells. Then, the cells were dividedly added at an amount of 0.3 cells per a well of the 96-well plate, and then the 96-well plates were sequentially prepared at an amount of 1 cell, 10 cells and more per a well, respectively. At this time, the clones, grown in the plate including the smallest amount of the cells, were selected and grown again, and the above-mentioned procedure was repeated, if necessary. Finally, the clone grown in the most diluted density of the plate was considered to be a monoclonal clone.

By carrying out the procedure, the monoclonal antibodies, finally proven to have an anti-D-dimer specificity, were named B2, C3, B4 and C5, respectively.

Example 3: Characterization of Prepared Monoclonal Antibodies B2-05

Figures 2, 3:
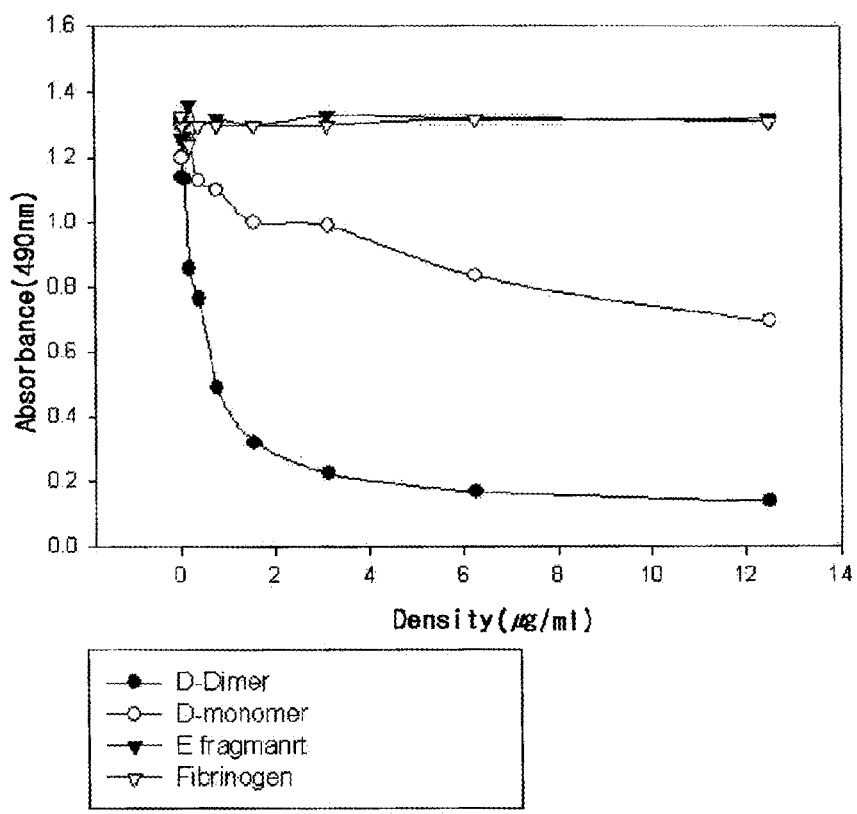
FIG. 2 is a table illustrating isotype of the monoclonal antibodies.
FIG. 3 is a diagram showing cross-reactivity of a monoclonal antibody B4 on a D-dimer.

In order to determine immunoglobulin antibody types of the monoclonal antibodies, a kit (Pierce) for determining mouse immunoglobulin type was used. Firstly, wells of ELISA plate were coated with an antigen, the purified monoclonal antibodies were added thereto, and rabbit-derived anti-mouse immunoglobulin antibodies, respectively, specific to the mouse immunoglobulin types were added, and then goat-derived anti-rabbit immunoglobulin antibodies to which horseradish peroxidase (HRP) binds were added to screen whether or not positive results are found in the monoclonal antibodies. As a result, it was confirmed that all the monoclonal antibodies are kappa light chains of IgG1, as shown in FIG. 2.

Example 4: Test of Antigen Specificity to B4 a. Determination of Antigen Specificity to Monoclonal Antibody B4

Figure 4:
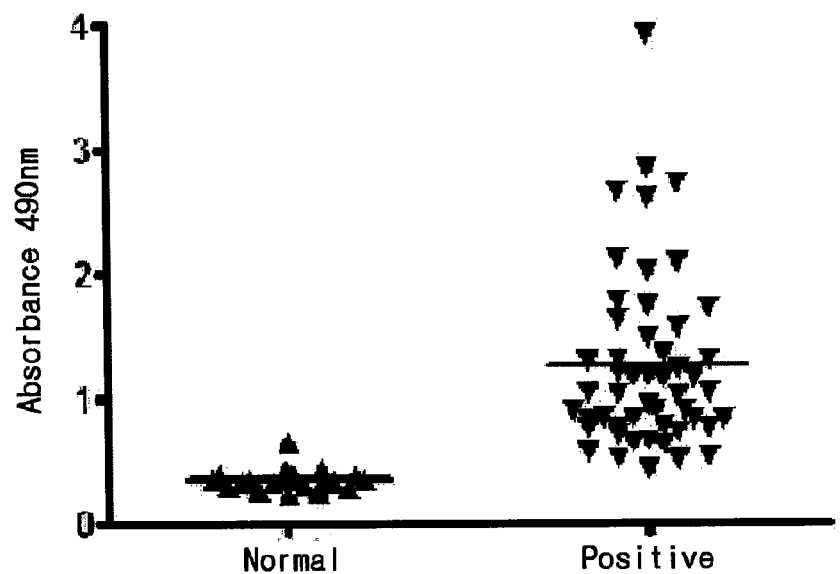
FIG. 4 is a diagram showing plasma test results of a normal human and a patient having a high level of D-dimer using monoclonal antibodies B4 and B2.

In order to determine antigen specificity to monoclonal antibody 134 using an enzyme-linked immunoassay, a competitive inhibition enzyme-linked immunosorbent assay (ELISA) was carried out. For this purpose, the human D-dimer prepared in Example 1 was thoroughly mixed in a coating buffer (0.1M Na-carbonate, pH 9.5), and the mixture was added at an amount of 1 µg to each well of a 96-well ELISA plate (Maxisorp, Nunc), and then reacted overnight at 4° C. The antigen coating solution was removed off, and a blocking buffer (1% bovine serum albumin/PBS) was added and kept at a room temperature for 2 hours. Then, the solution was removed off, and each 10 of the wells was washed with a PBST (prepared by adding 0.1% Tween 20 to phosphate-buffered saline) buffer. In order to confirm specificity of an antigen that reacts to the monoclonal antibody B4, 25 µg/ml of each of D-dimer, D monomer, E domain and fibrinogen was firstly reacted to monoclonal antibody B4 to which horseradish peroxidase (HRP) binds at 37° C. for 1 hours, respectively, and then the reaction solutions were added to the plates coated with D-dimer. In addition, the reaction solutions was further reacted at 37° C. for 1 hour, and removed off, and the plate was washed, and o-phenylenediamine (Sigma) which is a substrate of HRP, and hydrogen peroxide solution ($H_2O_2$) were sequentially added to confirm whether or not the specifically bound antibody is present in the culture solution. As a result, it was seen that the monoclonal antibody B4 has a high dissociation constant of $9.8 \times 10^{-10}$ M, and it was also seen that the monoclonal antibody B4 has a low reactivity of $5 \times 10^{-6}$ M to the D monomer and is specific to D-dimer exhibiting no cross reactivity to fibrinogen fragments such as fibrinogen, E domain (FIG. 4).

b. Determination of Antigen Specificity to Monoclonal Antibody Using Western Blotting In order to determine an antigen specificity to the monoclonal antibodies, D-dimer, D monomer, E domain and fibrinogen were electrophoresed on a SDS-PAGE gel, and the resultant gel was then transferred to 0.45 µm of a nitrocellulose membrane (Bio-rad) in a Iris-glycin-methanol buffer and blotted. In order to remove non-specific reaction products, the nitrocellulose membrane was blocked with 5% nonfat dry milk at room temperature for 2 hours, and then the monoclonal antibody B4 specific to D-dimer was diluted to a suitable density and reacted for 1 hour. Then, the nitrocellulose membrane was washed with a PBS buffer containing 1% Tween-20, and then an horseradish peroxidase (HRP) conjugated anti-mouse IgG antibody (Sigma) was diluted at a volumetric ratio of 1:2500 and reacted for 1 hour, and the reagents were removed off by washing the same volume of the PBS buffer, and developed with 4-chloro-1-naphthol and $H_2O_2$. As a result, it was found that the B4 reacts to only D-dimer.

Example 5: Identification of Fine Epitope to B4 a. Determination of Fine Epitope to B4

Figures 6, 7:
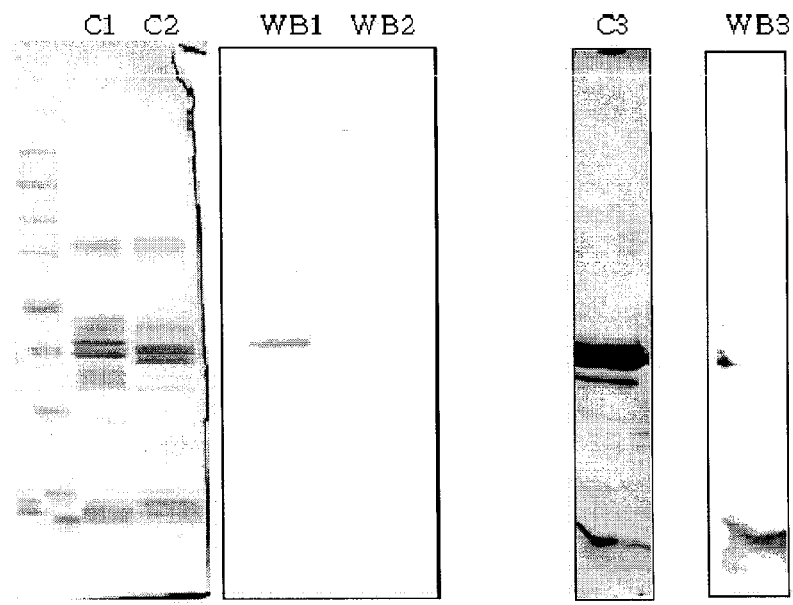
FIG. 6 is a photograph showing determination of an epitope recognized by the monoclonal antibody.
FIG. 7 is a diagram showing an epitope region of the monoclonal antibody B4 confirmed using an amino acid sequence analysis of 38 and 37 kDa fragments.

In order to determine a fine epitope to the monoclonal antibody B4 using D-dimer protein, D-dimer protein was degraded with various enzymes and a western blotting was carried out on the degradation products of D-dimer. The equivalent amount of D-dimer protein was degraded at a volumetric ratio of 1:10 to 1:100 with trypsin, chymotrypsin, pepsin and CNBr at 37 C for 30 minutes to 4 hours. Its degradation products were divided into two groups and electrophoresed in a non-reduced gel and a reduced gel, respectively. The resultant gels were transferred to nitrocellulose membranes, and then western blotting were carried out using the monoclonal antibody B4 in the same manner as described above in Example 4b. As a result, it was revealed that D-dimer protein and its fragments degraded by trypsin and chymotrypsin were recognized by the monoclonal antibody B4 in the non-reduced gel, but only the beta chain or the 38-Da fragment degraded by trypsin was recognized by the monoclonal antibody B4 in the reduced gel (C1 and WB1 in FIG. 6). Meanwhile it was revealed that the 37-kDa fragment degraded by chymotrypsin was not recognized (C2 and WB2 in FIG. 6). In order to determine from which site of the protein the reactivity difference is derived in the two fragments, an N-terminal amino acid sequence analysis and MS/MS analysis were carried out. As a result, it was found that C-terminuses of the two protein fragments were identical to each other, but their N-terminuses were different to each other, and therefore a peptide fragment consisting of 9 amino acid residues from the N-terminus of the beta chain, that is a B134~B142 fragment, was recognized by the monoclonal antibody B4, as shown in FIG. 7. Also, it was found that the 13-kDa fragment was recognized by the monoclonal antibody B4 even when the western blotting was carried out on the fragment degraded by the CNBr treatment (C3 and WB3 in FIG. 6), and a fine epitope of the monoclonal antibody B4 corresponds to the protein fragment consisting of amino acid sequences 124 to 214 of the alpha chain when the fragment was analyzed using the MS/MS analysis. It was found that the two sites of the protein fragments are portions of a string structure in which alpha, beta and gamma chains are twisted to each other, which are widely known as regions that are hidden in fibrinogen but newly exposed when fibrinogen is cut by plasmin after its crosslinking reaction (see Brown J. H., Proc. Natl. Acad. Sci. USA 2000 97: 85-90; Evers S. J., Biochemistry 1999 38(10): 2941-2946).

Example 6: Determination of D-Dimer Density in Human Plasma Using C3/B4

A density of D-dimer or fibrin degradation products containing D-dimer might be measured using the monoclonal antibody B4 specific to D-dimer. The measurement was carried out using a double antibody sandwich ELISA. A monoclonal antibody C3 was thoroughly mixed in a coating buffer (0.1M Na-carbonate, pH 9.5), and the resultant mixture was added at an amount of 1 μg to each of the 96-well ELISA plate (Maxisorp, Nunc), and then reacted overnight at 4° C. A non-coated antibody was removed off, and a blocking buffer (1% bovine serum albumin/PBS) was added and reacted at a room temperature for 2 hours, and then each of the wells was washed with a PBST (prepare by adding 0.1% Tween 20 to phosphate-buffered saline) buffer. Human plasma was diluted 20 times with the 1% bovine serum albumin/PBS buffer, added at an amount of 100 μl to each well, and then reacted at 37° C. for 1 hour. After the solution was reacted at 37° C. for 1 hour, the solution was removed off, and then each of the wells was washed 4 times with a washing solution. Then, D-dimer-specific monoclonal antibody B4 to which horseradish peroxidase (HRP) binds was diluted at 1:2000 with a 1% bovine serum albumin/PBS buffer, added at an amount of 100 μl to each well, and then further reacted at 37° C. for 1 hour. 0-phenylenediamine (Sigma) which is a substrate of I-IRP, and hydrogen peroxide solution ($H_2O_2$) were sequentially added to confirm whether or not the specifically bound antibody is present in the culture solution. As a result, absorbance of the culture solution was quantitatively increased according to the density of D-dimer in plasma of the patients, and therefore a patient group was distinguishable from a normal group (FIG. 4).

Example 7: Comparison Between Conventional Diagnosis Agent and ELISA Diagnosis Prepared Using C3/B4 a. Comparison Test Between DIC-Suspected Patient Group and Normal Group

Figure 5:
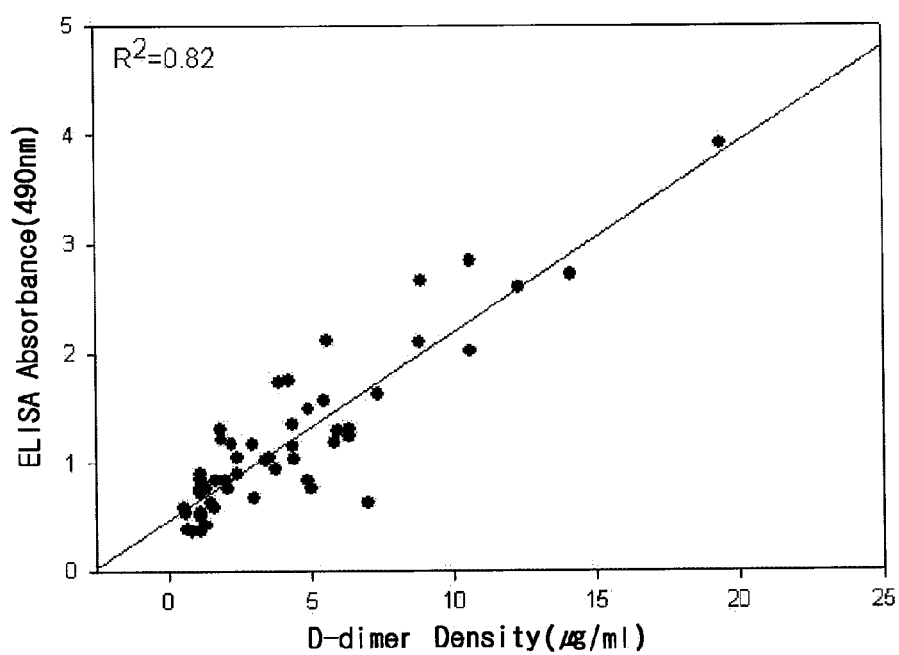
FIG. 5 is a diagram showing that a level of D-dimer in plasma from thrombosis-suspected patients is measured by an ELISA method using monoclonal antibodies C3/B4.
Figures 8, 9:
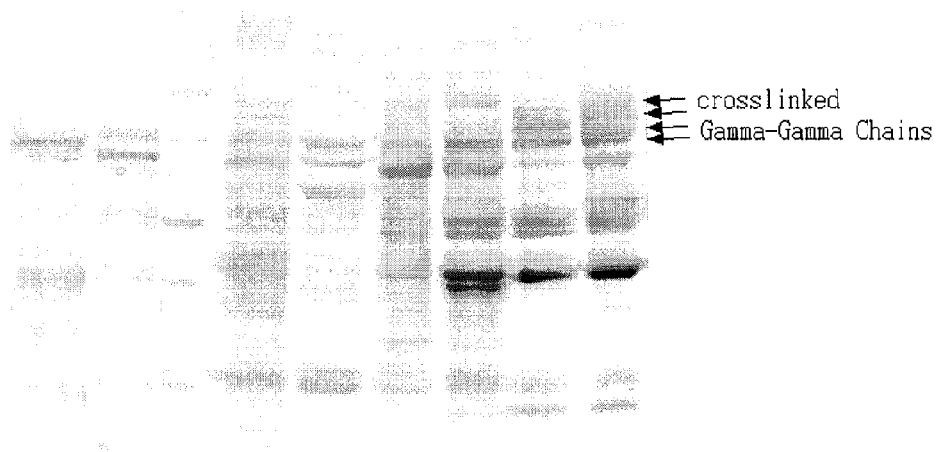
FIG. 8 is a diagram showing an SDS-electrophoretic result that the patient plasmas exhibiting different results in the ELISA method of the present invention and the commercially available diagnosis agent are passed through a column having each of the corresponding antibodies fixed therein, and then the resultant eluents are analyzed in an SDS-electrophoresis gel. Lanes #1, 2 and 3 represent the patient plasmas exhibiting the different results in the ELISA method, respectively, and Lane #4 represents the column eluents of the patient plasmas exhibiting the same results.
FIG. 9 is a table showing a profile that detection signals are increased when the undissolved cross-linked fibrin, which is present in the plasma from the disseminated intravascular coagulation (DIC)-suspected patients, is artificially degraded by adding plasmin.

A density of D-dimer in plasma of DIC-suspected patient group and a normal group was measured in the same manner as described above in Example 6, and a commercially available diagnosis agent (AGEN) was also tested according to the procedure as described in a manufacturer's manual, and then a linearity was plotted by comparing absorbances which are the test results of the patient samples (FIG. 5). As a result, it was revealed that the two measurement methods are tested using the same material, for example D-dimer, and also have a high correlation. However, the ELISA results of the present invention were measured at a very higher level than that of the commercially available diagnosis agent in the case of some DIC-suspected patients, but it was considered that the diagnostic results of the present invention is more reliable since all of the patient samples were obtained from patients who were proven to be acute DIC patients on the basis of partial thromboplastin time (PTT) delayed syndrome, a reduced amount of platelet and fibrinogen, a positive reaction of D-dimer, etc.

b. Difference Analysis from Commercial Diagnosis Agent using Monoclonal Antibodies DD3B6/22 and B4 Column This experiment was carried out in the case of the patients exhibiting the relatively high difference between the commercially available diagnosis agent and the ELISA method, as described above in Example 7. The monoclonal antibodies DD3B6/22 and B4 used for the commercially available diagnosis reagent were fixed to a sepharose resin, activated with N-hydroxysuccinimide (NHS), according to the van Sommeren's method to prepare columns, respectively. The three plasma (samples 1, 2 and 3 in FIG. 8 and FIG. 9) exhibiting the different results in Example 6 were passed through the column prepared thus, and then SDS-PAGE was carried out on the eluent fragments to confirm band patterns of D-dimer respectively recognized by the monoclonal antibodies. As shown in FIG. 8, bands of the cross-linked gamma-gamma-chains and the beta chains were clearly observed in the sample fragments 1, 2 and 3 eluted from the B4 column, while these bands were not present or rarely observed in the sample fragments eluted from the DD3B6/22 column. The presence of the gamma-gamma chain having a molecular weight of at least 80 kDa means that the cross-linked fibrin is not degraded completely. Even in the case of the plasma sample 4 having the nearly same ELISA results in the above-mentioned two methods, band patterns of the sample fragments eluted from the two columns were confirmed in the same manner as described above. In this case, the similar band patterns were observed in the two columns. From these results, it was seen that, since fibrin degradation products were not present as the completely degraded D-dimer but the cross-linked fibrin or its derivatives in plasma of some patients, an amount of D-dimer was detected at a lower level than that of the actual D-dimer in the case of the DD3B6/22 that does not recognize the cross-linked fibrin or its derivatives, or in the case of the diagnosis agent using the DD3B6/22 (see Carl E. D., Thromb Haemost 2001 85:671-678).

c. ELISA Signal Change in Plasmin-Treated Plasma of DIC-Suspected Patient

The partially degraded cross-linked fibrin or its derivatives were artificially degraded by treating the patient plasma samples 1, 2, 3 and 4 with plasmin according to the same method as described in Example 1, and then a density of D-dimer in the plasma samples was measured again using the ELISA diagnosis agent. As shown in FIG. 9, it was revealed that ELISA signals were significantly increased when the plasmin-treated patient plasma samples 1, 2 and 3 were tested using the commercially available diagnosis agent, while ELISA signals were similar or reduced when the plasmin-treated patient plasma samples 1, 2 and 3 were tested using the C3/B4 ELISA method of the present invention. Accordingly, the ELISA diagnostic method of the present invention has a performance to detect D-dimer as well as the cross-linked fibrin and its derivatives, and therefore may be especially useful to diagnose a population having a large amount of the high molecular weight cross-linked fibrin in plasma, for example patients suffering from thrombosis for a long time, or patients who are subject to the early thrombus treatment.

d. Clinical Trial on Rapid Kit Prepared Using Monoclonal Antibodies C3/B4

A D-dimer Rapid kit was prepared according to a conventional method using the monoclonal antibodies (mAb) C3 and B4 of the present invention. As shown in FIG. 9, it was seen that the mAb of the present invention more specifically binds to the untreated high molecular weight (HMW) fibrin, compared to other commercially available kits. In addition, it was known the diagnosis kit (AGEN) more sensitively reacts to the HMW-fibrin and the diagnosis kit (Stago) more sensitively reacts to the LMW-fibrin [Dempfle C E, et al., *Thromb Haemost* 2001; 85: 671-8]. In the present invention, D-dimer levels in the four clinical samples of the present invention were overestimated and reduced after the plasmin treatment, compared to the diagnosis kit (Stago). On the contrary, D-dimer levels were increased by the pre-treatment of the plasma samples with plasmin in the diagnosis kit (Stago). According to the Fibrin Assay Comparison Trial (FACT) study by Demple C E, et al. [Thromb haemost, 2001, 85: 671-8; and Thromb Haemost 2001, 86: 1204-9], and a report by Gaffney et al. [Gaffney P J, et al., *Br J Haematol* 1995; 90:187-94], it was found that Fibrin Degradation Products (FnDPs) produced under a flowing condition is mainly composed of HMW-derivatives rather than D-dimer fragments, and HMW-fibrin oligomers are major targets for analyzing D-dimer in the clinical samples. In this aspect, the mAb of the present invention may be used as a reliable and improved method capable of detecting low molecular weight (LMW) dimer as well as HMW-fibrin without any of their cross reactivity in the clinical trial.

Example 8. Preparation of Label (Monoclonal Anti-D-Dimer Antibody Conjugated Metallic Gold Sol Label)

Gold sol particles were prepared according to a procedure well known in the art; such as Luevering (U.S. Pat. No. 4,313,734) the contents of which are incorporated herein by reference. The pH of gold sol is adjusted to 7.5. Mouse anti-D-dimer B2 antibody (final conc. 20 µg/mL) is added to 50 mL of gold sol solution and stirred well for 30 min at ambient temperature. To this solution, 1.5 mL of 15% bovine serum albumin is added, and the solution is continuously stirred for approximately 15 min at ambient temperature. Colloidal gold-monoclonal antibody conjugate is recovered by centrifugation at 10,000 rpm in GSA rotor for 1 hr, discarding the supernatant and suspending the resultant pellet in 25 mL of 2% bovine serum albumin in deionized water, pH 7.5. The suspension is then spun down at 10,000 rpm for 1 hr in GSA rotor. The supernatant once again is discarded and the pellet suspended in 6 mL of 2% bovine serum albumin in deionized water, pH 7.5.

Example 9. Preparation of Biotinylated Monoclonal Anti-D-Dimer C3 Antibodies

The antibody solution is added into 50 mM sodium carbonate, pH 8.5 to obtain a final concentration of 1 mg/mL and then Biotinamidocaproate N-hydroxysuccinimide ester (Sigma) in N,N-DiMethylFormamide (5 mg/mL) is added slowly while stirring (final concentration of biotin: 37.5 µg/mL). The solution is stirred well for 30 min at ambient temperature. Free Biotinamidocaproate N-Hydroxysuccinimide ester is removed by dialyzing the resulting solution in PBS buffer.

The above described Monoclonal Anti-D-dimer Antibody conjugated metallic gold sol label and Biotinylated monoclonal anti-D-dimer C3 Antibody can be used in the preparation of dye zone (indicator pad) and reservoir pad as shown below. It is noted that the pair of B4 and C3 can be similarly biotinylated or conjugated to metallic gold sol label. For example, one of B4 and C3 can be conjugated to a metallic gold label while the other of the two can be biotinylated.

Example 10. Preparation of Test Strips a. Immobilized Substance for Test Band and Pre-absorption of Labeled Antibody Double sided transparent tape (305 mm×25 mm size) is attached 20 mm from the bottom of a thin plastic plate (305 X.62 mm). A piece or strip of nitrocellulose membrane is cut to 305 mm X.25 mm size and attached directly on top of the double sided tape. An assay indicia zone of immobilized test line for D-dimer is defined on the membrane by impregnating 35 µL of a solution of 2 mg/mL streptoavidin. A control line is defined on the membrane by impregnating 1 mg/mL of sheep or goat anti-mouse IgG antibody about 10 mm apart upward from the test line. After printing the assay indicia zones, the membrane is dried at ambient temperature for approximately 12 hours. The base and wicking membrane can be stored in a desiccator until further processed.

b. Preparation of Dye Zone (Indicator Pad) and Reservoir (Filter) Pad

Glass fiber sheet is pretreated with a solution of 0.3% BSA, 0.3% β-lactose, 0.2% casein, and 0.05% TWEEN-20, 0.7% Glycine in 10 mM sodium phosphate buffer and then air dried at room temperature. This pretreated glass fiber sheet is used to prepare indicator pad and reservoir filter pad. The indicator pad is prepared from the pretreated glass fiber sheet measuring 8 mm×305 mm by wetting with a solution of antibody conjugated metallic gold sol prepared in Example 1—the colloidal gold mouse anti-D-dimer B2 antibody conjugate—in 10 mM sodium phosphate, pH 7.5, 0.25% casein, 0.5% trehalose, 0.15% glucose, 20 mM EDTA, 0.1% sodium azide and drying. The pad is stored dry in a desiccator until use. The reservoir filter pad is prepared from the pretreated glass fiber sheet by spraying a predetermined amounts of biotin and monoclonal anti-D-dimer C3 antibody conjugated solution. The pad is then dried.

c. Unitized Point-of-Care Test Device

The indicator pad prepared in 3b is attached to a plastic base such that 1 mm overlaps with the bottom of nitrocellulose membrane. A blood separation filter pad is located below the indicator pad and then the reservoir filter pad is attached adjacent to the blood separation filter pad. The plastic plate then is cut into a plurality of strips 62 mm in length and 6.5 mm in width so that each contains a linear array of nitrocellulose membrane, indicator pad, blood separation filter pad and reservoir filter pad. The test strip thus prepared was assembled into a plastic cassette housing in such a way that the sample application well is located right above the blood separation filter pad and the result reading window is right above the assay indicia zone enabling visual or reader reading of the results when the assay is performed. The Device was sealed in an aluminum foil pouch to protect from atmospheric moisture during storage over the life of the test kit.

Example 11. Serum or Plasma Sample Assay Protocol and Result

Patient blood sample for analysis was collected into a tube containing K2-EDTA or Sodium Citrate as anti-coagulant. The tube was centrifuged and the supernatant plasma layer is collected for assay. To begin the assay, 130 µL of EDTA or Citrate plasma sample was applied to reservoir filter pad. A detectable signal began to appear in the assay indicia zone after about 5 min. The assay sensitivity was 250 ng/mL. The result was read visually in 10 to 15 minutes: a clear visible test line at the assay indicia zone and control line indicate the detection of D-dimer above the assay sensitivity limit of 250 ng/mL. A positive result was an indication of DVT (Deep Vein Thrombosis) and/or PE (Pulmonary Embolism) that may require further imaging diagnosis and medical intervention. For assay using serum sample, serum sample was used in the assay following the same assay procedures as in plasma use assay.

Example 12. Whole Blood Assay

The whole blood assay protocol was the same as for the EDTA or Citrate plasma assay. When 130 µL of EDTA or citrate whole blood was applied to reservoir filter pad, the red blood cells were filtered and the plasma migrates upward in the same way as with the plasma or serum assay in example 4. Detectable signal began to appear in the assay indicia zone in about 5 min. The assay sensitivity was 250 ng/mL.

The result was read visually in 10 to 15 minutes: a clear visible test line at the assay indicia zone and control line indicated the detection of D-dimer above the assay sensitivity limit of 250 ng/mL. A positive result was an indication of DVT (Deep Vein Thrombosis) and/or PE (Pulmonary Embolism) that may require further imaging diagnosis and medical intervention.

Example 13. Quantitative Assay Using a Desktop Reader

Using either serum or plasma sample or whole blood samples as in Examples 11 and 12, the assay is conducted the same way except the result is read using a portable desktop reader. The desktop reader is a reflectance absorption reader that takes images of the test window of the device and converts the signal intensity into concentration of marker, D-dimer, detected by the assay. The reader is pre-programmed for such reading and conversion into concentration using a standard curve and a conversion equation.

a. Calibration of Standard Curve in Absorption Reading

Figure 10:
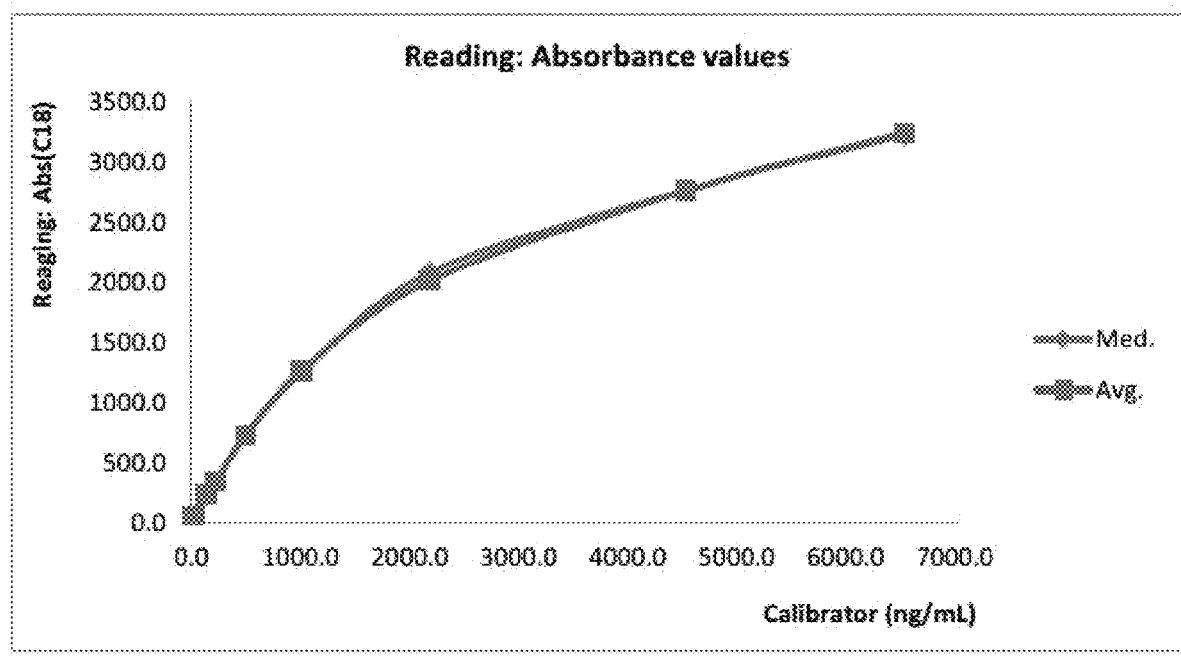
FIG. 10 illustrates the absorbance reading at different concentrations of D-dimer in plasma.

Plasma calibrators having concentration range covering the assay dynamic range of 0 to 6,000 ng/mL in eight (8) levels of concentration of D-dimer in plasma were prepared. Each level of calibrator was assayed in 20 replicates as shown in the table below. The results in absorbance reading demonstrated good assay reproducibility as shown in FIG. 10.

Calibration for DD2L111
1. Calibrator: DD-2L09-08-D
2. Test date: Dec. 5~06, 2012
3. Reader: 0808 & 0409
5. Result
1) ABS Values

| | Vial | | | | | | | |
|---|---|---|---|---|---|---|---|---|
| | 0 | 100 | 200 | 500 | 1000 | 2000 | 4000 | 6000 |
| | | | | SF Assigned value | | | | |
| | 22.7 | 134.5 | 219.9 | 498.0 | 1008.7 | 2184.2 | 4534.9 | 6539.0 |
| 1 | 57.0 | 232.2 | 290.7 | 726.4 | 1073.9 | 2251.4 | 2791.9 | 3324.8 |
| 2 | 40.2 | 221.0 | 296.4 | 715.5 | 1219.1 | 1779.6 | 2724.7 | 3775.0 |
| 3 | 53.7 | 225.5 | 255.9 | 526.1 | 1347.2 | 1893.1 | 2785.7 | 3313.8 |
| 4 | 39.0 | 284.9 | 254.2 | 721.9 | 1320.1 | 1435.1 | 2999.1 | 3153.8 |
| 5 | 37.5 | 224.1 | 389.6 | 792.9 | 1234.9 | 1997.3 | 2725.4 | 3257.7 |
| 6 | 41.5 | 242.0 | 324.8 | 728.2 | 1244.2 | 2177.6 | 2891.6 | 3400.5 |
| 7 | 53.2 | 238.6 | 364.9 | 737.7 | 1406.7 | 1976.9 | 2590.8 | 3666.4 |
| 8 | 88.5 | 258.4 | 329.8 | 660.7 | 1263.2 | 1885.3 | 2721.0 | 3235.1 |
| 9 | 75.3 | 239.2 | 358.1 | 759.1 | 1492.1 | 2140.7 | 2752.4 | 3378.6 |
| 10 | 33.1 | 227.3 | 419.3 | 710.2 | 1345.0 | 2064.6 | 2956.2 | 3062.1 |
| 11 | 53.2 | 225.1 | 321.0 | 742.6 | 1231.7 | 2090.9 | 2725.9 | 3510.4 |
| 12 | 44.0 | 230.5 | 358.7 | 712.0 | 1219.5 | 2068.3 | 2786.2 | 3226.2 |
| 13 | 38.6 | 253.7 | 364.0 | 681.0 | 1220.9 | 2095.9 | 2853.3 | 3067.7 |
| 14 | 49.7 | 216.3 | 304.3 | 786.6 | 1265.5 | 2038.4 | 2752.3 | 3219.0 |
| 15 | 95.5 | 188.3 | 373.9 | 718.9 | 1263.5 | 2098.5 | 2503.0 | 3431.8 |
| 16 | 67.5 | 257.3 | 340.3 | 725.7 | 1199.1 | 2183.0 | 2596.7 | 2881.5 |
| 17 | 55.8 | 246.3 | 317.1 | 816.8 | 1250.7 | 2201.1 | 3054.3 | 3184.0 |
| 18 | 69.8 | 253.6 | 387.3 | 729.8 | 1185.6 | 1647.7 | 2845.3 | 3011.3 |
| 19 | 58.5 | 219.5 | 373.3 | 656.1 | 1284.0 | 2090.6 | 2830.4 | 2656.0 |
| 20 | 27.8 | 227.7 | 346.8 | 778.7 | 1210.4 | 2140.5 | 2417.5 | 3189.9 |
| Med. | 53.2 | 231.3 | 343.6 | 726.0 | 1247.4 | 2079.5 | 2769.1 | 3230.7 |
| Avg. | 54.0 | 235.6 | 338.5 | 721.3 | 1263.9 | 2012.8 | 2765.2 | 3247.3 |
| Sd | 18.0 | 20.3 | 43.7 | 61.6 | 88.0 | 201.0 | 156.7 | 254.6 |
| CV | N/A | 8.6 | 12.9 | 8.5 | 7.0 | 10.0 | 5.7 | 7.8 |

Figure 11:
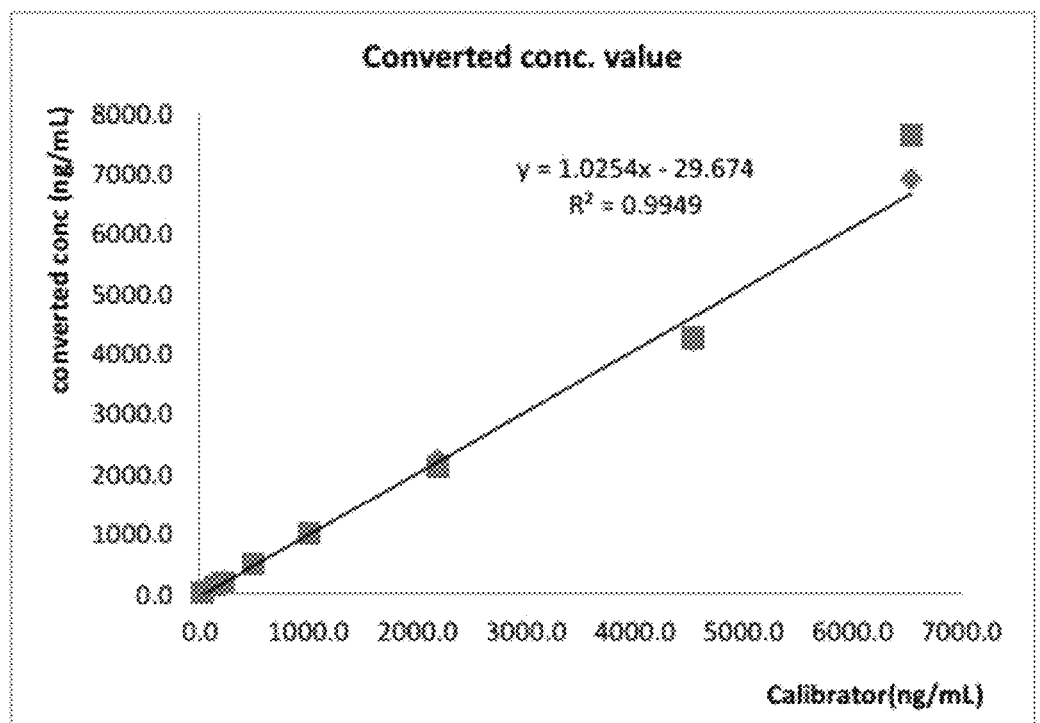
FIG. 11 illustrates converted concentration value which demonstrates good assay reproducibility.

Overall CV (100~4000) 8.8 b. Calibration of Standard Curve in Absorption Reading and Conversion to Concentration The plasma calibrators with concentration range covering the assay dynamic range of 0 to 6,000 ng/mL were prepared, in eight (8) levels of concentration of D-dimer in plasma. Each level of calibrator was assayed in 20 replicates as shown in the table below. The results in absorbance reading were further converted in accordance to the standard curve constructed for concentration vs. signal intensity of the test line. These results also demonstrated good assay reproducibility as shown in FIG. 11.

2) Backfit Data (Converted Concentration Data)
5 PLs

| Coef a | Coef b | Coef c | Coef d | Coef g |
|---|---|---|---|---|
| 4287.5 | −1.058 | 2544 | 17.361 | 0.956 |

| | | | | Vial | | | |
|---|---|---|---|---|---|---|---|
| 0 | 100 | 200 | 500 | 1000 | 2000 | 4000 | 6000 |
| | | | | SF Assigned value | | | |
| 22.7 | 134.5 | 219.9 | 498.0 | 1008.7 | 2184.2 | 4534.9 | 6539.0 |

| | | | | | | | | |
|---|---|---|---|---|---|---|---|---|
| 1 | 25.0 | 138.1 | 177.5 | 504.2 | 820.7 | 2620.1 | 4328.6 | 7783.4 |
| 2 | 14.5 | 130.7 | 181.4 | 495.3 | 972.2 | 1708.3 | 4054.6 | 15979.6 |
| 3 | 23.0 | 133.7 | 154.0 | 345.9 | 1117.4 | 1896.6 | 4302.4 | 7674.5 |
| 4 | 13.7 | 173.5 | 152.8 | 500.6 | 1085.7 | 1223.9 | 5344.4 | 6334.3 |
| 5 | 12.8 | 132.7 | 246.1 | 560.4 | 989.5 | 2084.9 | 4057.6 | 7159.2 |
| 6 | 15.3 | 144.7 | 200.8 | 505.8 | 999.7 | 2452.1 | 4781.3 | 8596.1 |
| 7 | 22.7 | 142.4 | 228.7 | 513.7 | 1188.8 | 2046.8 | 3571.4 | 12952.4 |
| 8 | 45.0 | 155.6 | 204.3 | 450.6 | 1020.9 | 1883.2 | 4040.2 | 6966.0 |
| 9 | 36.6 | 142.8 | 223.9 | 531.7 | 1296.3 | 2372.3 | 4164.8 | 8346.6 |
| 10 | 10.0 | 134.9 | 267.3 | 490.9 | 1114.7 | 2215.4 | 5109.2 | 5718.1 |
| 11 | 22.7 | 133.4 | 198.2 | 517.8 | 986.0 | 2268.4 | 4059.3 | 10046.8 |
| 12 | 16.9 | 137.0 | 224.4 | 492.4 | 972.7 | 2222.8 | 4304.4 | 6892.9 |
| 13 | 13.5 | 152.5 | 228.1 | 467.0 | 974.1 | 2278.6 | 4600.2 | 5753.6 |
| 14 | 20.5 | 127.6 | 186.8 | 555.1 | 1023.4 | 2163.7 | 4176.5 | 6833.6 |
| 15 | 49.4 | 109.2 | 235.0 | 498.1 | 1021.2 | 2284.0 | 3292.4 | 8972.1 |
| 16 | 31.7 | 154.9 | 211.6 | 503.7 | 950.6 | 2464.2 | 3591.2 | 4732.4 |
| 17 | 24.3 | 147.5 | 195.5 | 581.0 | 1007.0 | 2504.5 | 5670.2 | 6558.2 |
| 18 | 33.2 | 152.4 | 244.5 | 507.1 | 936.1 | 1508.9 | 4563.6 | 5413.7 |
| 19 | 26.0 | 129.7 | 234.6 | 447.0 | 1044.3 | 2267.8 | 4496.0 | 3797.1 |
| 20 | 6.7 | 135.1 | 216.1 | 548.3 | 962.8 | 2371.8 | 3044.7 | 6603.7 |
| Med. | 22.7 | 137.6 | 213.8 | 504.0 | 1003.3 | 2245.3 | 4233.6 | 6929.5 |
| Avg. | 23.2 | 140.4 | 210.6 | 500.8 | 1024.2 | 2141.9 | 4277.1 | 7655.7 |
| Sd | 11.4 | 13.5 | 30.3 | 50.0 | 100.5 | 349.4 | 646.8 | 2791.3 |
| CV | 49.0 | 9.6 | 14.4 | 10.0 | 9.8 | 16.3 | 15.1 | 36.5 |

Overall CV (100–4000) 12.5

Example 14. Immunochemical Assay Device

Figure 12:
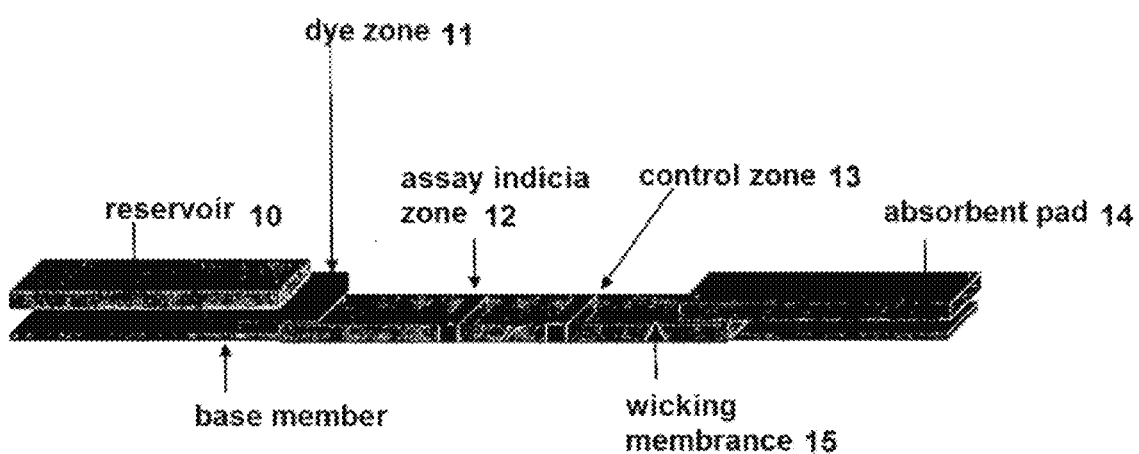
FIG. 12 illustrates an exemplary detection device.
Figure 13A:
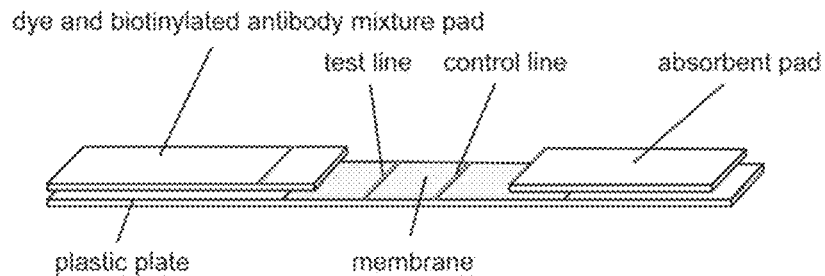
FIGS. 13a, 13b, and 13c illustrate three exemplary configurations of the detection device. (a) 1-pad system; (b) 2-pad system; and (c) 3-pad system.
Figure 13B:
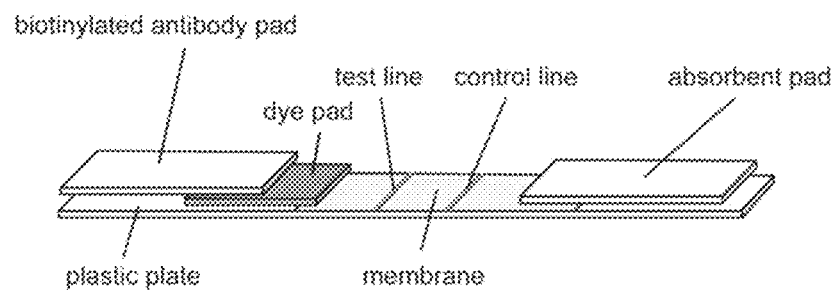
Figure 13C:
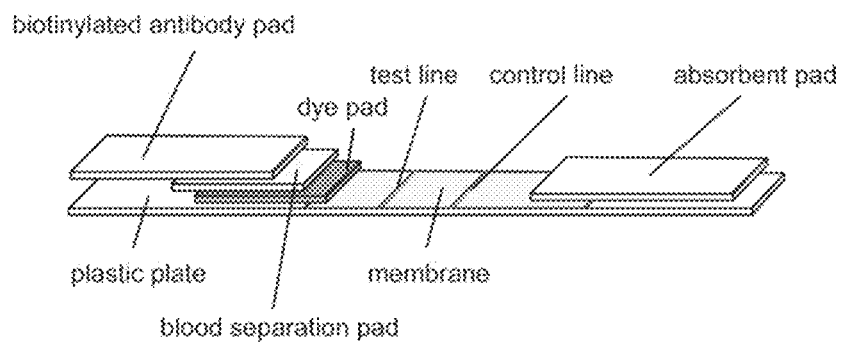

In an exemplary device as shown in FIG. 12, the dye zone 11 is separate and distinct from the reservoir pad 10, and wicking membrane 15, and interposed between and contiguous with the wicking membrane 15, and the reservoir 10. The dye zone has impregnated therein a labelled immunochemical component capable of binding to D-dimer and/or cross-linked fibrin. in a sample to form an immuno-complex. The dye zone is operable to permit passage of any specific immuno-complex to the wicking membrane 15, while impeding passage of larger components then contained in the sample; and at least one immobilized substance disposed in at least one assay indicia zone 12 of the wicking membrane 15 downstream of the dye zone, the immobilized substance being operable to bind a specific immuno-complex contained in the sample to form the assay indicia. Various modifications of the device can be implemented, For example, the reservoir, the dye zone, and the wicking membrane can be configured as a. three vertical pad system. Alternatively, they can be aligned adjacent to each other. Further, the reservoir and the dye zone can be integrated into a single pad. Any additional zone (e.g. blood filter zone) can be included in the device. For example, a filter pad can be placed under or adjacent to the dye zone. The reservoir, the dye zone and the blood filter zone can be configured as a 3-pad, 2-pad, or 1-pad structure. FIG. 13 illustrate three exemplary configurations (1-pad, 2-pad and 3-pad systems), Of course, within each exemplified configuration, the alignment and spatial relationship between individual structural components may vary. For example, the dye pad may be placed between the biotinylated antibody pad and the blood separation pad in the 3-pad system. The dye pad may also be placed above the other two pads.

An exemplary embodiment, which is not meant to define or constrain the device and method described herein, is performed as follows. A test sample, such as, but not limited to, animal serum is contacted with an immunochemical component conjugated to a first label on the filter zone at the sample application point on the test device. The immunochemical component is capable of specifically binding to D-dimer and/or cross-linked fibrin in the sample to form an immuno-complex. The immuno-complex and other components are chromatographed along the length of the absorbent pad (such as, but not limited to, a nitrocellulose membrane). The indicia zone contains an immobilized substance which binds to the label conjugated to the immunochemical component. If a second immunochemical component specifically binding to D-dimer and/or cross-linked fibrin is present in the filter zone, a second label conjugated to the second immunochemical component can provide detectable signal. When the resulting immuno-complex reaches the indicia zone, the signal can be detected visually or with a reading device (e.g. a fluorescence scanner). The excess labeled second immunochemical component will flow, via capillary action, to the control zone 13 which is separated from the assay indicia 12. When an immobilized control capture reagent binds to the labeled second immunochemical component, a positive signal is generated. A further embodiment disclosed herein incorporates the quantitation of D-dimer and/or cross-linked fibrin in the test sample, as determined by the intensity of the signal generated relative to an intensity of signals generated in a standard curve. Further, the device and the method described herein are applicable to other immunological analysis, detection, and/or quantification of biological markers of interest.

As described above, the anti-D-dimer monoclonal antibody of the present invention may be more useful to diagnose DIC-suspected patients, compared to the conventional antibodies specific only to D-dimer, since the anti-D-dimer monoclonal antibody is a kappa light chain of an IgG1 type, and specifically reacts to a human D-dimer but does not exhibit a cross reactivity to the other structurally similar proteins, and also specifically reacts to a high molecular weight cross-linked fibrin containing a sugar epitope. The monoclonal antibody of the present invention may be effectively used as a diagnosis agent for screening and detecting D-dimer in tissues and blood vessels, and in particular useful to diagnose diseases such as disseminated intravascular coagulation (DIC), deep vein thrombosis (DVT), pulmonary embolism (PE), various thrombosis since the monoclonal antibody is manufactured with a high activity and specifically reacts to D-dimer.

Example 15

Preparation of Label (monoclonal anti-NT-pro-BNP antibody conjugated to metallic colloidal gold sol) for use in 2-in-1 assays for D-dimer and NT-por-BNP assay in one test strip device.

Monoclonal mouse anti-NT-pro-BNP antibody (6G11) were conjugated to metallic colloidal gold sol as in Example 8 to prepare the labeled antibody for use in the 2-in-1 assay.

Example 16. Preparation of Test Strip for the 2-in-1 Assay for D-Dimer and NT-Pro-BNP a. Immobilized substance for test band and control band in the assay indicia zone.

The test strip was prepared in a procedure similar as in example 10. On the test strip, the indicia zone has two test bands: 1 and 2. Band 1 is printed with polyclonal goat anti-NT-pro-BNP antibodies. Band 2 is printed at about 10 mm downstream of band 1 with streptavidin for D-dimer assay as in example 10. In addition, there is a third line for control band, about 10 mm apart from the second band, printed with polyclonal sheep anti-mouse antibody.

b. Preparation of Dye Zone (Indicator Pad) and Reservoir Filter Pad for the 2-in-1 Assay: D-Dimer and NT-Pro-BNP in One.

Mixture of two indicators of a colloidal Gold conjugate of monoclonal anti-NT-proBNP and a colloidal Gold conjugate of monoclonal anti-D-dimer B2 were mixed with a proper portion of Biotin conjugated monoclonal anti-D-dimer C3 antibodies prepared in a procedure similar as in Example 9. Dry filter pad of reagents consist of the three reagent mixtures were prepared in a procedure similar as in Example 10b.

Figure 14A:
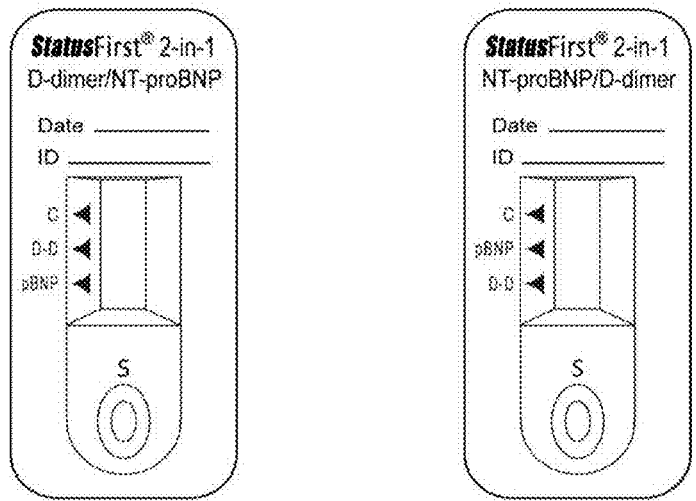
FIG. 14(a) shows a diagram of new devices.
Figure 14B:
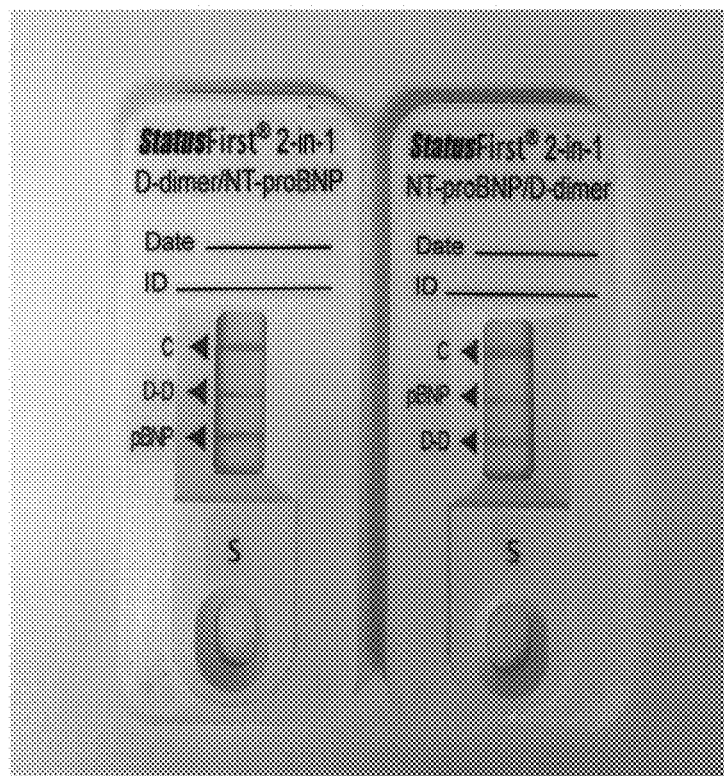
FIG. 14(b) shows device after sample testing.

FIG. 14 shows exemplary assay device for detecting D-dimer and NT-pro-BNP. FIG. 14(a) shows new devices. FIG. 14(b) shows a device after sample testing.

c. Preparation of Filter Pads in 1 Pad, 2-Pad and 3-Pad Optional System.

Filter pads to be placed on the test strip that can function as unitized test device include i). a pad for sample absorption and release; ii) a pad for blood filtration; and iii) at least a pad for dry indicators such as colloidal gold conjugates and biotinylated antibodies. Exemplary pad configurations are shown in the example drawings for 1-, 2- and/3-pad system. It is often practiced to minimize the number of different pads by combining reagents or two function in one such as blood separation and reagent pad.

Figure 15A:
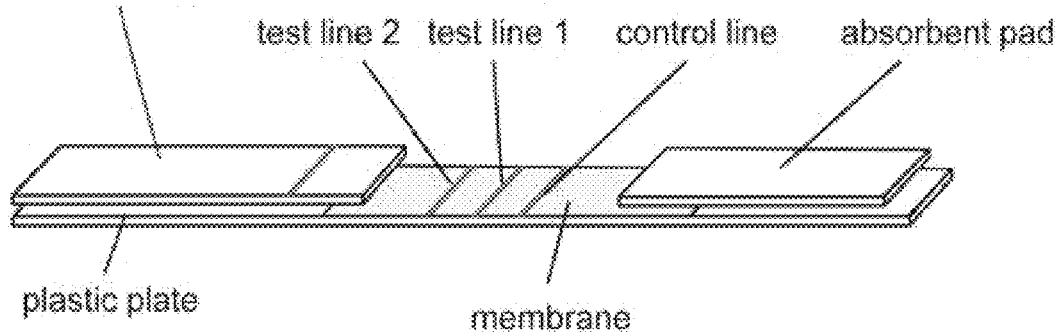
FIG. 15(a) is a one-pad system.
Figure 15B:
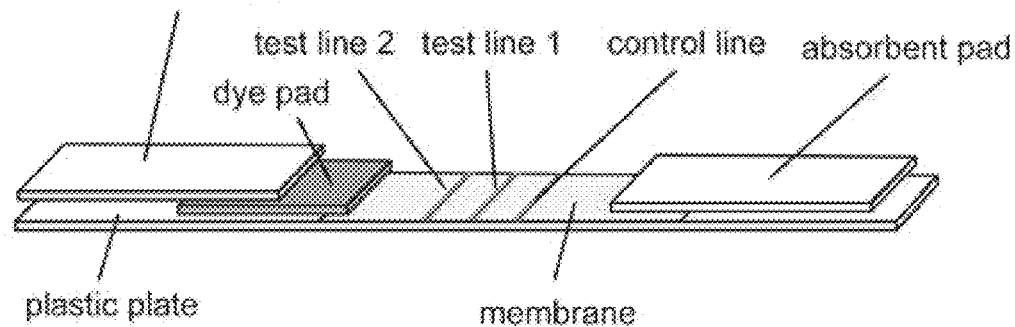
FIG. 15(b) is a two-pad system.
Figure 15C:
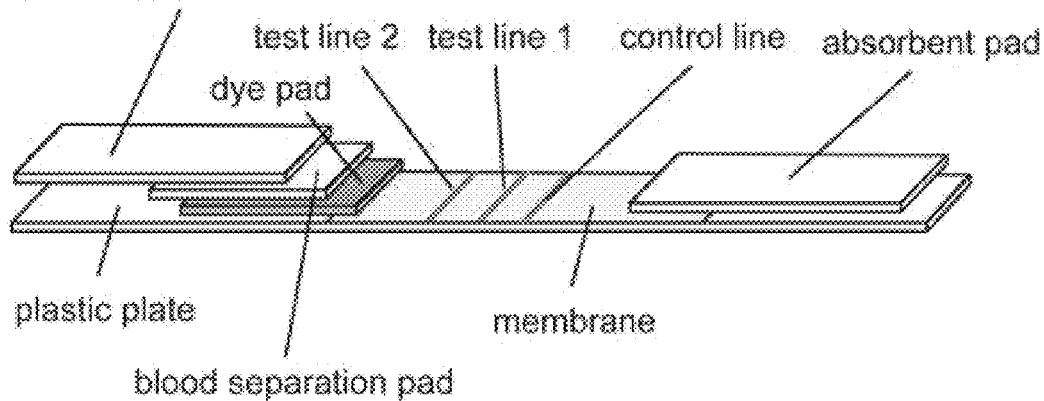
FIG. 15(c) is a three-pad system.

FIG. 15 shows exemplary configurations for assay devices with various pad configurations: FIG. 15(a) is a one-pad system; FIG. 15(b) is a two-pad system; FIG. 15(c) is a three-pad system.

d. Unitized Point-of-Care Test Device.

As in Example 10c, unitized point-of-care, ready to use device was prepared having one 2-in-1 test strips in the plastic device for D-dimer and NT-pro-BNP test in one simple test.

The device was used in assay for calibration of standard curve constration for quantitative analysis (e.g. assay of whole blood, serum or plasma samples).

e. Quantitative determination assay using a desktop reader.

As in Example 13, quantitative determination for concentration of analytes such as D-dimer and NT-pro-BNP was made in one sample in one step assay.

f. Calibration of Standard Curve in Absorbance Value and Automatic Conversion to Concentration Using Desktop Reader.

Different Example 13 and 13a. a sample was analyzed here to determine two markers/targets in the same sample, instead of just one marker in the Example 13.

g. The Followings Data are Shown as Summary of Assay, Assay Calibration Results for D-Dimer and NT-Pro-BNP, Absorbance Curves, Standard Curves for the Two Assay from which we can Obtain the Concentration Directly from the Reader.

1. D-Dimer Antibody
Indicator: monoclonal anti-D-dimer B2
Capture: monoclonal anti-D-dimer C3
2. NT-proBNP Antibody
Indicator Mouse anti-NT-proBNP (6G11)
Capture C3: Goat anti-NTproBNP (amino acids 31-51)
Membrane: Polyclonal goat anti-NT-proBNP for NT-proBNP and streptavidin for D-dimer are immobilized on test area 1 and 2
Mixture of Gold conjugates: monoclonal anti-NT-proBNP and monoclonal anti-D-dimer B2
Biotin conjugate: monoclonal anti-D-dimer C3
3. Assay Sensitivity
D-dimer: 250 ng/mL
NT-proBNP: 125 pg/mL (<75 yrs), 450 pg/mL (75+)
4. Measuring Range
D-dimer: 60-5000 ng/mL
NT-proBNP: 30-5000 pg/mL
5. Calibration
D-dimer: same as single device
NT-proBNP: same as single device The assay was analyzed for serum, plasma sample or whole blood samples. The result was read using a portable reader. The reader was a reflectance absorption reader that took images of the test window of the device and converted the signal intensity into concentration of marker, D-dimer and NT-proBNP, detected by the assay. The reader was pre-programmed for such reading and conversion into concentration using a standard curve and a conversion equation.

Calibration of Standard Curve in absorption reading and conversion to concentration:

D-dimer

The eight (8) levels of concentration of D-dimer in plasma were prepared. Each level of calibrator was assayed in 10 replicates.

NT-proBNP

The nine (9) levels of concentration of NT-proBNP in plasma were prepared. Each level of calibrator was assayed in 10 replicates.

Calibration Data
Calibration for DF8F110
Calibrator:
D-dimer calibrator: L DD-8B20-08-D
NT-proBNP calibrator: 07CHCC0058E
Absorbance Values
NT-proBNP

| | Vial | | | | | | | | |
|---|---|---|---|---|---|---|---|---|---|
| | 25 | 50 | 100 | 200 | 500 | 1000 | 2000 | 4000 | 6000 |
| | | | | | Roche | | | | |
| | 24.5 | 55.0 | 98.0 | 201.0 | 508.0 | 989.5 | 1995.5 | 3868.5 | 6075.5 |
| 1 | 64.6 | 112.9 | 161.9 | 327.4 | 754.9 | 1264.1 | 1754.7 | 2331.9 | 2763.7 |
| 2 | 61.0 | 114.3 | 164.7 | 311.0 | 621.7 | 1331.9 | 1751.4 | 2489.7 | 2743.3 |
| 3 | 82.1 | 126.5 | 229.4 | 308.2 | 766.3 | 1313.6 | 1866.2 | 2244.4 | 2981.6 |

-continued

| | Vial | | | | | | | | |
|---|---|---|---|---|---|---|---|---|---|
| | 25 | 50 | 100 | 200 | 500 | 1000 | 2000 | 4000 | 6000 |
| | | | | | Roche | | | | |
| | 24.5 | 55.0 | 98.0 | 201.0 | 508.0 | 989.5 | 1995.5 | 3868.5 | 6075.5 |
| 4 | 60.4 | 109.6 | 205.4 | 354.2 | 789.8 | 1127.8 | 1765.8 | 2422.3 | 2710.6 |
| 5 | 88.9 | 116.7 | 232.4 | 393.1 | 772.8 | 1122.5 | 1703.9 | 2283.4 | 2692.5 |
| 6 | 66.0 | 97.3 | 229.6 | 319.5 | 716.6 | 1237.6 | 1880.8 | 2488.5 | 3025.1 |
| 7 | 69.7 | 120.6 | 231.1 | 355.0 | 706.2 | 1288.0 | 1549.4 | 2228.1 | 2756.3 |
| 8 | 46.8 | 104.7 | 204.4 | 318.2 | 659.7 | 1270.7 | 1828.7 | 2361.4 | 2692.3 |
| 9 | 88.6 | 90.7 | 200.2 | 330.0 | 705.7 | 1144.9 | 1767.4 | 2155.1 | 2815.4 |
| 10 | 63.9 | 103.8 | 222.8 | 352.6 | 700.2 | 1104.7 | 1620.7 | 2461.4 | 2654.1 |
| Med. | 65.3 | 111.3 | 214.1 | 328.7 | 711.4 | 1250.8 | 1760.2 | 2346.6 | 2749.8 |
| Avg. | 69.2 | 109.7 | 208.2 | 336.9 | 719.4 | 1220.6 | 1748.9 | 2346.6 | 2783.5 |
| Sd | 13.5 | 10.8 | 26.6 | 26.5 | 52.8 | 86.7 | 103.5 | 117.9 | 124.7 |
| CV | N/A | 9.9 | 12.8 | 7.9 | 7.3 | 7.1 | 5.9 | 5.0 | 4.5 |

Overall CV (100~4000) 7.7

D-Dimer

| | vial | | | | | | | |
|---|---|---|---|---|---|---|---|---|
| | 0 | 100 | 200 | 500 | 1000 | 2000 | 4000 | 6000 |
| | | | | SF assigned value | | | | |
| | 15.4 | 98.2 | 207.4 | 523.9 | 1022.2 | 2065.5 | 3921.6 | 6460.9 |
| 1 | 24.2 | 90.0 | 244.0 | 563.2 | 925.9 | 1592.2 | 2164.2 | 2621.2 |
| 2 | 17.3 | 122.1 | 206.9 | 512.2 | 917.4 | 1441.8 | 1971.2 | 2433.8 |
| 3 | 28.7 | 99.0 | 239.2 | 585.3 | 925.0 | 1491.5 | 2208.1 | 2424.8 |
| 4 | 16.3 | 105.8 | 257.9 | 559.3 | 817.3 | 1510.3 | 2145.6 | 2375.1 |
| 5 | 34.7 | 135.7 | 224.6 | 499.8 | 880.8 | 1639.8 | 2042.3 | 2497.9 |
| 6 | 16.5 | 86.7 | 207.8 | 470.7 | 918.7 | 1560.7 | 1917.6 | 1919.7 |
| 7 | 9.8 | 93.0 | 198.9 | 599.1 | 901.5 | 1357.1 | 2207.2 | 2460.3 |
| 8 | 8.0 | 92.3 | 190.5 | 500.4 | 881.4 | 1317.1 | 1970.3 | 2510.4 |
| 9 | 33.2 | 110.8 | 225.5 | 493.2 | 915.6 | 1408.4 | 2210.4 | 2504.3 |
| 10 | 17.7 | 129.2 | 185.5 | 446.4 | 794.4 | 1431.5 | 2149.1 | 2154.8 |

-continued

| | vial | | | | | | | |
|---|---|---|---|---|---|---|---|---|
| | 0 | 100 | 200 | 500 | 1000 | 2000 | 4000 | 6000 |
| | | | | SF assigned value | | | | |
| | 15.4 | 98.2 | 207.4 | 523.9 | 1022.2 | 2065.5 | 3921.6 | 6460.9 |
| Med. | 17.5 | 102.4 | 216.2 | 506.3 | 908.6 | 1466.6 | 2147.4 | 2447.0 |
| Avg. | 20.6 | 106.5 | 218.1 | 522.9 | 887.8 | 1475.0 | 2098.6 | 2390.2 |
| SD | 9.2 | 17.5 | 24.1 | 50.8 | 46.4 | 103.3 | 112.5 | 204.8 |
| CV | N/A | 16.4 | 11.0 | 9.7 | 5.2 | 7.0 | 5.4 | 8.6 |

Overall CV (100~4000) 9.1

Figure 16:
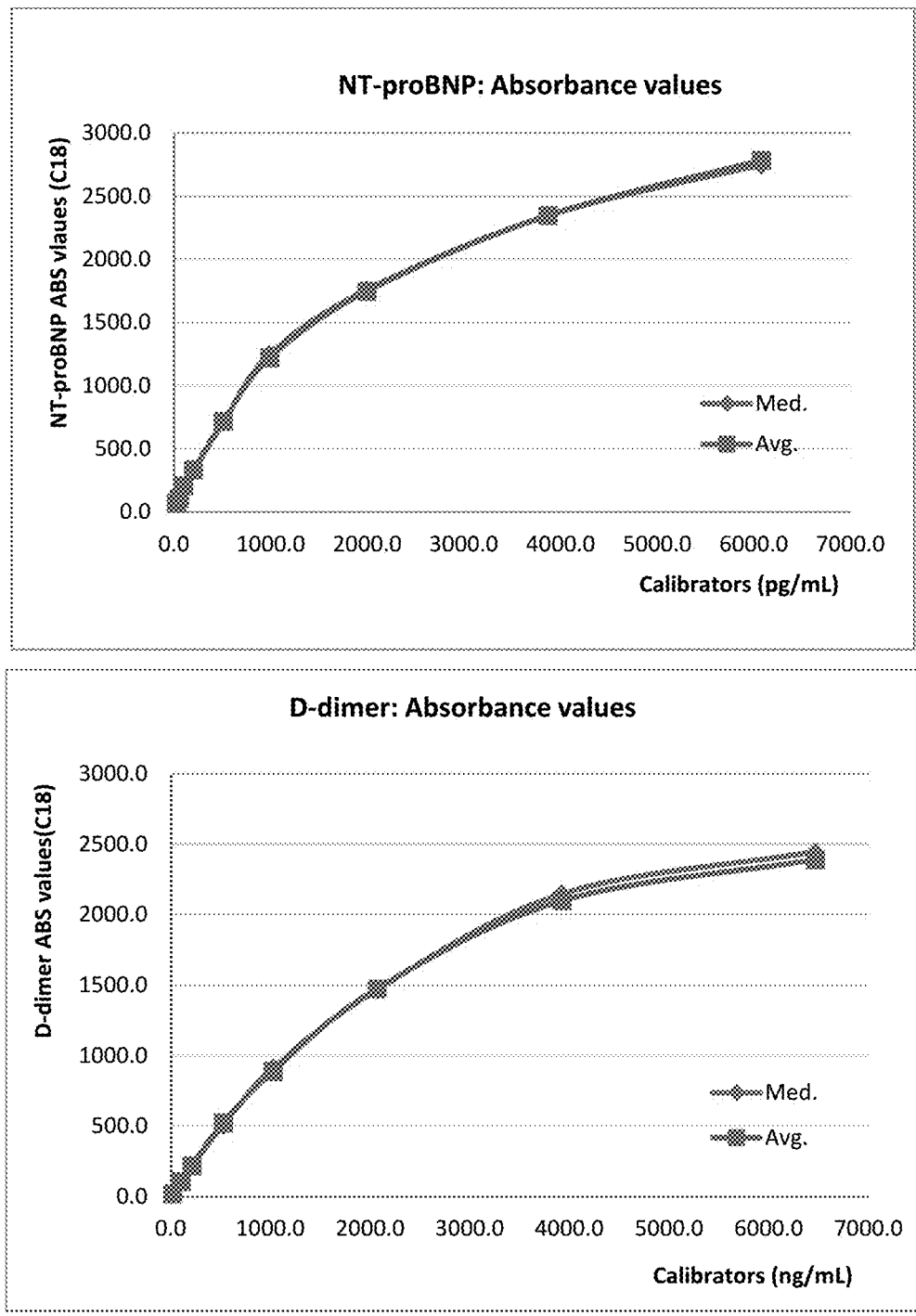
FIG. 16 shows the calibration curves of NT-proBNP and D-dimer.
Figure 17:
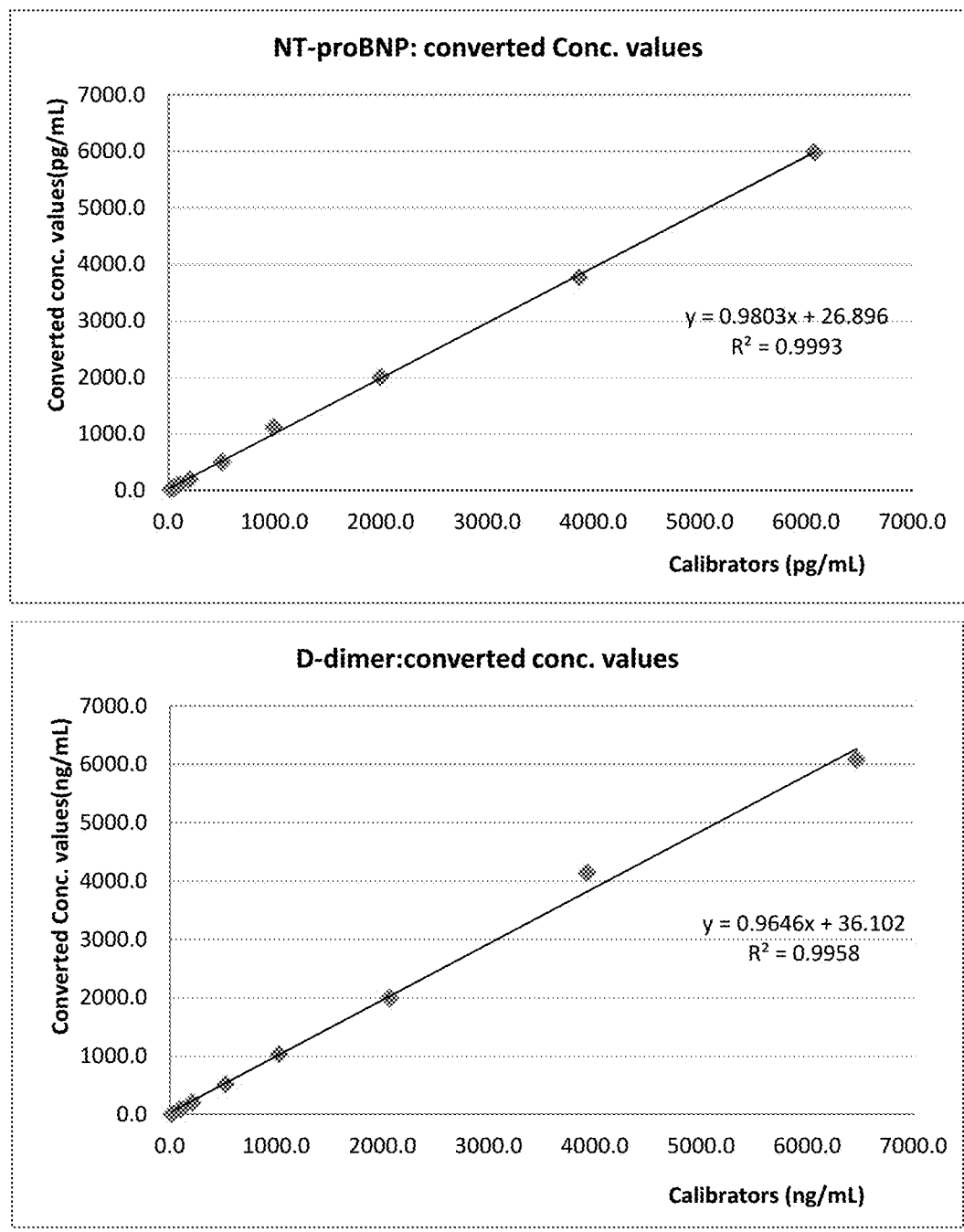
FIG. 17 shows the standard curves of NT-proBNP and D-dimer (converted conc. values).

The Calibration Curves of NT-proBNP and D-dimer are shown in FIG. 16. The Standard Curves of NT-proBNP and D-dimer (converted conc. Values) are shown in FIG. 17.
Backfit Data (Converted Concentration Data)
NT-proBNP 5 PLs

| Coef a | Coef b | Coef c | Coef d | Coef g |
|---|---|---|---|---|
| 4012.05 | −0.945 | 2659 | 15.772 | 0.995 |

| | Vial | | | | | | | | |
|---|---|---|---|---|---|---|---|---|---|
| | 25 | 50 | 100 | 200 | 500 | 1000 | 2000 | 4000 | 6000 |
| | | | | | Roche | | | | |
| | 24.5 | 55.0 | 98.0 | 201.0 | 508.0 | 989.5 | 1995.5 | 3868.5 | 6075.5 |
| 1 | 24.9 | 52.4 | 81.9 | 191.9 | 547.4 | 1143.4 | 2001.7 | 3709.0 | 6089.2 |
| 2 | 22.9 | 53.2 | 83.7 | 180.4 | 424.9 | 1241.9 | 1994.7 | 4415.5 | 5938.2 |
| 3 | 34.6 | 60.4 | 125.0 | 178.4 | 558.5 | 1214.8 | 2256.1 | 3374.2 | 8088.9 |
| 4 | 22.6 | 50.4 | 109.4 | 211.1 | 581.6 | 960.8 | 2025.8 | 4095.6 | 5707.6 |
| 5 | 38.5 | 54.6 | 126.9 | 239.7 | 564.9 | 954.0 | 1894.5 | 3518.8 | 5584.6 |
| 6 | 25.6 | 43.3 | 125.1 | 186.0 | 510.9 | 1106.3 | 2291.4 | 4409.2 | 8598.7 |
| 7 | 27.7 | 56.9 | 126.1 | 211.7 | 501.3 | 1177.4 | 1597.6 | 3315.6 | 6034.1 |
| 8 | 15.3 | 47.6 | 108.7 | 185.4 | 458.7 | 1152.7 | 2167.3 | 3830.2 | 5583.3 |
| 9 | 38.3 | 39.5 | 106.0 | 193.8 | 500.8 | 982.6 | 2029.3 | 3066.6 | 6495.4 |
| 10 | 24.5 | 47.0 | 120.6 | 209.9 | 495.7 | 931.7 | 1729.6 | 4277.3 | 5335.2 |
| Med. | 25.3 | 51.4 | 115.0 | 192.8 | 506.1 | 1124.8 | 2013.8 | 3769.6 | 5986.2 |
| Avg. | 27.5 | 50.5 | 111.3 | 198.8 | 514.5 | 1086.6 | 1998.8 | 3801.2 | 6345.5 |
| Sd | 7.5 | 6.3 | 17.0 | 19.1 | 49.4 | 117.9 | 217.6 | 483.9 | 1108.3 |
| CV | N/A | 12.5 | 15.2 | 9.6 | 9.6 | 10.8 | 10.9 | 12.7 | 17.5 |

Overall CV (100~4000) 11.5

D-Dimer 5 PLS

| | Coef a | Coef b | Coef c | Coef d | Coef g |
|---|---|---|---|---|---|
| | 3116.24 | −1.39 | 3231 | 0.000025 | 0.696 |

| | vial | | | | | | |
|---|---|---|---|---|---|---|---|
| | 0 | 100 | 200 | 500 | 1000 | 2000 | 4000 | 6000 |
| | | | | SF assigned value | | | | |
| | 15.4 | 98.2 | 207.4 | 523.9 | 1022.2 | 2065.5 | 3921.6 | 6460.9 |
| 1 | 21.3 | 83.2 | 236.6 | 587.9 | 1058.2 | 2279.2 | 4226.3 | 8028.1 |
| 2 | 15.0 | 114.3 | 198.7 | 528.4 | 1046.1 | 1943.8 | 3401.7 | 5965.8 |
| 3 | 25.4 | 91.8 | 231.7 | 614.1 | 1056.9 | 2049.5 | 4452.0 | 5890.4 |
| 4 | 14.2 | 98.5 | 251.0 | 583.4 | 907.5 | 2090.8 | 4135.9 | 5500.4 |
| 5 | 31.0 | 127.7 | 216.7 | 514.2 | 994.5 | 2395.7 | 3678.0 | 6554.9 |
| 6 | 14.3 | 80.0 | 199.6 | 481.1 | 1048.0 | 2205.0 | 3210.3 | 3217.4 |
| 7 | 8.4 | 86.1 | 190.7 | 630.7 | 1023.5 | 1773.9 | 4447.5 | 6197.9 |
| 8 | 6.8 | 85.4 | 182.2 | 514.9 | 995.3 | 1697.6 | 3398.4 | 6681.7 |
| 9 | 29.5 | 103.3 | 217.6 | 506.6 | 1043.6 | 1875.3 | 4464.1 | 6619.4 |
| 10 | 15.4 | 121.3 | 177.1 | 453.7 | 877.0 | 1922.5 | 4152.6 | 4180.4 |
| Med. | 15.2 | 95.1 | 208.2 | 521.6 | 1033.6 | 1996.7 | 4144.2 | 6081.9 |
| Avg. | 18.1 | 99.1 | 210.2 | 541.5 | 1005.1 | 2023.3 | 3956.7 | 5883.7 |
| SD | 8.4 | 17.0 | 24.5 | 59.0 | 64.1 | 223.4 | 487.8 | 1353.6 |
| CV | N/A | 17.1 | 11.7 | 10.9 | 6.4 | 11.0 | 12.3 | 23.0 |

Overall CV (100~4000) 11.6

We claim:

1. An immunochemical assay device for detecting a target of interest in a fluid sample, comprising:
   a base member; an array disposed on said base member, said array comprising:
   a. a reservoir pad having sufficient porosity and volume to receive and contain a fluid sample upon which an assay is to be performed, wherein said reservoir pad is impregnated therein a first immunochemical antibody conjugated to a first label, said first immunochemical antibody capable of specifically binding to a target of interest in said sample to form an immuno-complex;
   b. a wicking membrane disposed distally to said reservoir pad, said wicking membrane having sufficient porosity and volume to absorb a substantial proportion of the sample received in said reservoir pad; and
   c. a dye zone impregnated therein a second immunochemical antibody conjugated to an indicia label, said second immunochemical antibody capable of specifically binding to the target of interest, wherein the indicia label is different from the first label; and
   d. an assay indicia zone disposed in said wicking membrane, wherein an immobilized substance is disposed in said assay indicia zone of said wicking membrane downstream of said reservoir pad for providing an assay indication, said immobilized substance being specific and binding to said first label in the immuno-complex to form assay indicia,
   wherein said target of interest is D-dimer and/or cross-linked fibrin.

2. The assay device of claim 1, further comprising a control zone disposed in said wicking membrane downstream of said indicia zone, wherein a third immunochemical antibody is immobilized in said control zone, and binding of said third immobilized immunochemical antibody to the second immunochemical antibody conjugated to the indicia label and unbound to the target of interest forms control assay indicia.

3. The assay device of claim 1, wherein said first immunochemical antibody conjugated to the first label and said second immunochemical antibody conjugated to the indicia label are each an antibody and independently bind to a site including
   a) amino acid residues 134th to 142nd from N-terminal region of a beta-chain, set forth in SEQ ID NO: 1; or
   b) amino acid residues 124th to 214th from N-terminal region of a beta-chain, set forth in SEQ ID NO: 2.

4. The assay device of claim 2, wherein the second immunochemical component is a mouse antibody, wherein said third immunochemical antibody is a sheep or goat anti-mouse IgG antibody.

5. The assay device of claim 1, wherein said first label is biotin and said immobilized substance is avidin.

6. The assay device of claim 1, wherein said indicia label is selected from the group consisting of metallic colloidal gold sol, fluorescent dye, and chromogenic dye encapsulated micro-particles or fibers.

7. The assay device of claim 1, further comprising a filter zone disposed on said base member, said filter zone permitting passage of any specific immuno-complex in said sample, but impeding passage of larger components contained in said sample.

8. The assay device of claim 1, wherein said wicking membrane comprises microporous membrane material selected from the group consisting of nylon, cellulosic material, polysulfone, polyvinylidene difluoride, glass fiber, polyester, and combinations thereof.

9. The assay device of claim 1, wherein the wicking membrane comprises nitrocellulose.

10. The assay device of claim 1, wherein said dye zone is separate and distinct from said reservoir pad and said wicking membrane, and interposed between and in fluid communication with said wicking membrane and said reservoir pad.

11. The assay device of claim 1, wherein said dye zone and said reservoir pad are integrated into a single pad.

12. A system for detecting a target of interest in a fluid sample, comprising the assay device of claim 1, and a detector for detecting said indicia label in said assay indicia.

13. The system of claim 12, where said detector comprises a camera for recording the image and/or intensity of said signals.

14. The system of claim 12, wherein said detector is capable of wirelessly transmitting said signals to a processor.

15. A method of detecting a target of interest, comprising:
a) depositing a fluid sample to the reservoir pad of the assay device of claim 1;
b) maintaining said assay device under conditions which are sufficient to allow said target of interest to bind to said first immunochemical antibody conjugated to the first label, forming a specific binding complex, and to allow said fluid to transport said specific binding complex by capillary action through said membrane strip to said indicia zone;
c) maintaining said assay device under conditions which are sufficient to allow said specific binding complex in said fluid to bind to said immobilized substance; and
d) detecting a signal indicating the presence of the target of interest, wherein said target of interest is D-dimer and/or cross-linked fibrin.

16. The method of claim 15, further comprising comparing the signal with a standard indicative of normal level of said target of interest to determine a disease associated with abnormal level of said target of interest or a risk of having the disease.

17. The method of claim 15, further comprising comparing the signal with a standard indicative of normal level of D-dimer and/or cross-linked fibrin, and wherein a rise in the level of TD-dimer and/or cross-linked fibrin is indicative of thrombosis disease or a risk of having the thrombosis disease.

18. The method of claim 17, wherein the thrombosis disease is selected from the group consisting of disseminated intravascular coagulation (DIC), deep vein thrombosis (DVT), and pulmonary embolism (PE).

19. The method of claim 15, further comprising transmitting said signal wirelessly for processing.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Homo sapiens

<400> SEQUENCE: 1

Asp Asn Glu Asn Val Val Asn Glu Tyr
1               5

<210> SEQ ID NO 2
<211> LENGTH: 91
<212> TYPE: PRT
<213> ORGANISM: Homo sapiens

<400> SEQUENCE: 2

Asp Asn Thr Tyr Asn Arg Val Ser Glu Asp Leu Arg Ser Arg Ile Glu
1               5                   10                  15

Val Leu Lys Arg Lys Val Ile Glu Lys Val Gln His Ile Gln Leu Leu
                20                  25                  30

Gln Lys Asn Val Arg Ala Gln Leu Val Asp Met Lys Arg Leu Glu Val
            35                  40                  45

Asp Ile Asp Ile Lys Ile Arg Ser Cys Arg Gly Ser Cys Ser Arg Ala
    50                  55                  60

Leu Ala Arg Glu Val Asp Leu Lys Asp Tyr Glu Asp Gln Gln Lys Gln
65                  70                  75                  80

Leu Glu Gln Val Ile Ala Lys Asp Leu Leu Pro
                85                  90

<210> SEQ ID NO 3
<211> LENGTH: 50
<212> TYPE: PRT
<213> ORGANISM: homo sapiens

<400> SEQUENCE: 3

Leu Lys Asp Leu Trp Gln Lys Arg Gln Lys Gln Val Lys Asp Asn Glu
1               5                   10                  15

Asn Val Val Asn Glu Tyr Ser Ser Glu Leu Glu Lys His Gln Leu Tyr
                20                  25                  30

Ile Asp Glu Thr Val Asn Ser Asn Ile Pro Thr Asn Leu Arg Val Leu
            35                  40                  45

Arg Ser
    50

```
<210> SEQ ID NO 4
<211> LENGTH: 50
<212> TYPE: PRT
<213> ORGANISM: Homo sapiens

<400> SEQUENCE: 4

Leu Lys Asp Leu Trp Gln Lys Arg Gln Lys Gln Val Lys Asp Asn Glu
1               5                   10                  15

Asn Val Val Asn Glu Tyr Ser Ser Glu Leu Glu Lys His Gln Leu Tyr
            20                  25                  30

Ile Asp Glu Thr Val Asn Ser Asn Ile Pro Thr Asn Leu Arg Val Leu
        35                  40                  45

Arg Ser
    50

<210> SEQ ID NO 5
<211> LENGTH: 37
<212> TYPE: PRT
<213> ORGANISM: Homo sapiens

<400> SEQUENCE: 5

Asp Asn Glu Asn Val Val Asn Glu Tyr Ser Ser Glu Leu Glu Lys His
1               5                   10                  15

Gln Leu Tyr Ile Asp Glu Thr Val Asn Ser Asn Ile Pro Thr Asn Leu
            20                  25                  30

Arg Val Leu Arg Ser
        35

<210> SEQ ID NO 6
<211> LENGTH: 28
<212> TYPE: PRT
<213> ORGANISM: Homo sapiens

<400> SEQUENCE: 6

Ser Ser Glu Leu Glu Lys His Gln Leu Tyr Ile Asp Glu Thr Val Asn
1               5                   10                  15

Ser Asn Ile Pro Thr Asn Leu Arg Val Leu Arg Ser
            20                  25
```